(12) United States Patent
Shuster et al.

(10) Patent No.: US 7,739,917 B2
(45) Date of Patent: Jun. 22, 2010

(54) PIPE FORMABILITY EVALUATION FOR EXPANDABLE TUBULARS

(75) Inventors: Mark Shuster, Houston, TX (US); Lev Ring, Houston, TX (US)

(73) Assignee: Enventure Global Technology, LLC, Houston, TX (US)

(*) Notice: Subject to any disclaimer, the term of this patent is extended or adjusted under 35 U.S.C. 154(b) by 0 days.

(21) Appl. No.: 10/528,498

(22) PCT Filed: Aug. 18, 2003

(86) PCT No.: PCT/US03/25667
§ 371 (c)(1),
(2), (4) Date: Nov. 8, 2005

(87) PCT Pub. No.: WO2004/027392
PCT Pub. Date: Apr. 1, 2004

(65) Prior Publication Data
US 2006/0112768 A1    Jun. 1, 2006

Related U.S. Application Data

(60) Provisional application No. 60/412,653, filed on Sep. 20, 2002.

(51) Int. Cl.
*G01D 7/02* (2006.01)
*G01N 3/08* (2006.01)

(52) U.S. Cl. .......................... 73/789; 73/834

(58) Field of Classification Search ............. 420/89–97, 420/104–112; 73/834, 788–789, 862.391, 73/796
See application file for complete search history.

(56) References Cited

U.S. PATENT DOCUMENTS

| 46,818 A | 3/1865 | Patterson |
|---|---|---|
| 331,940 A | 12/1885 | Bole |

(Continued)

FOREIGN PATENT DOCUMENTS

AU    767364    2/2004

(Continued)

OTHER PUBLICATIONS

Liao et al. "Characterization of Ceramic Matrix Composite Tubes Under Uniaxial/Biaxial Monotonic and Cyclic Loading" Multiaxial Fatigue and Deformation Testing Techniques, ASTM STP1280, Published 1997, pp. 224-240.*

(Continued)

*Primary Examiner*—Lisa M Caputo
*Assistant Examiner*—Jonathan Dunlap
(74) *Attorney, Agent, or Firm*—Conley Rose, P.C.

(57) ABSTRACT

A method of testing a tubular member and selecting tubular members for suitability for expansion by subjecting a representative sample the tubular member to axial loading, stretching at least a portion of the tubular member through elastic deformation, plastic yield and to ultimate yield, and based upon changes in length and area calculating an expandability coefficient indicative of expandability of the tubular members and selecting tubular members with relatively high coefficients indicative of good expandability.

45 Claims, 2 Drawing Sheets

U.S. PATENT DOCUMENTS

| | | |
|---|---|---|
| 332,184 A | 12/1885 | Bole |
| 341,237 A | 5/1886 | Healey |
| 519,805 A | 5/1894 | Bavier |
| 802,880 A | 10/1905 | Phillips, Jr. |
| 806,156 A | 12/1905 | Marshall |
| 958,517 A | 5/1910 | Mettler |
| 984,449 A | 2/1911 | Stewart |
| 1,166,040 A | 12/1915 | Burlingham |
| 1,233,888 A | 7/1917 | Leonard |
| 1,494,128 A | 5/1924 | Primrose |
| 1,589,781 A | 6/1926 | Anderson |
| 1,590,357 A | 6/1926 | Feisthamel |
| 1,597,212 A | 8/1926 | Spengler |
| 1,613,461 A | 1/1927 | Johnson |
| 1,756,531 A | 4/1930 | Aldeen et al. |
| 1,880,218 A | 10/1932 | Simmons |
| 1,981,525 A | 11/1934 | Price |
| 2,046,870 A | 7/1936 | Clasen et al. |
| 2,087,185 A | 7/1937 | Dillom |
| 2,122,757 A | 7/1938 | Scott |
| 2,145,168 A | 1/1939 | Flagg |
| 2,160,263 A | 5/1939 | Fletcher |
| 2,187,275 A | 1/1940 | McLennan |
| 2,204,586 A | 6/1940 | Grau |
| 2,211,173 A | 8/1940 | Shaffer |
| 2,214,226 A | 9/1940 | English |
| 2,226,804 A | 12/1940 | Carroll |
| 2,246,038 A | 6/1941 | Graham |
| 2,273,017 A | 2/1942 | Boynton |
| 2,293,938 A * | 8/1942 | Dunn et al. ................. 148/320 |
| 2,301,495 A | 11/1942 | Abegg |
| 2,305,282 A | 12/1942 | Taylor, Jr. et al. |
| 2,371,840 A | 3/1945 | Otis |
| 2,383,214 A | 8/1945 | Prout |
| 2,447,629 A | 8/1948 | Beissinger et al. |
| 2,500,276 A | 3/1950 | Church |
| 2,546,295 A | 3/1951 | Boice |
| 2,583,316 A | 1/1952 | Bannister |
| 2,609,258 A | 11/1952 | Taylor, Jr. et al. |
| 2,627,891 A | 2/1953 | Clark |
| 2,647,847 A | 8/1953 | Black et al. |
| 2,664,952 A | 1/1954 | Losey |
| 2,691,418 A | 10/1954 | Connolly |
| 2,723,721 A | 11/1955 | Corsette |
| 2,734,580 A | 2/1956 | Layne |
| 2,796,134 A | 6/1957 | Binkley |
| 2,812,025 A | 11/1957 | Teague et al. |
| 2,877,822 A | 3/1959 | Buck |
| 2,907,589 A | 10/1959 | Knox |
| 2,919,741 A | 1/1960 | Strock et al. |
| 2,929,741 A | 1/1960 | Strock et al. |
| 3,015,362 A | 1/1962 | Moosman |
| 3,015,500 A | 1/1962 | Barnett |
| 3,018,547 A | 1/1962 | Marskell |
| 3,039,530 A | 6/1962 | Condra |
| 3,067,801 A | 12/1962 | Sortor |
| 3,067,819 A | 12/1962 | Gore |
| 3,068,563 A | 12/1962 | Reverman |
| 3,104,703 A | 9/1963 | Rike et al. |
| 3,111,991 A | 11/1963 | O'Neal |
| 3,167,122 A | 1/1965 | Lang |
| 3,175,618 A | 3/1965 | Lang et al. |
| 3,179,168 A | 4/1965 | Vincent |
| 3,188,816 A | 6/1965 | Koch |
| 3,191,677 A | 6/1965 | Kinley |
| 3,191,680 A | 6/1965 | Vincent |
| 3,203,451 A | 8/1965 | Vincent |
| 3,203,483 A | 8/1965 | Vincent |
| 3,209,546 A | 10/1965 | Lawton |
| 3,210,102 A | 10/1965 | Joslin |
| 3,233,315 A | 2/1966 | Levake |
| 3,245,471 A | 4/1966 | Howard |
| 3,270,817 A | 9/1966 | Papaila |
| 3,297,092 A | 1/1967 | Jennings |
| 3,326,293 A | 6/1967 | Skipper |
| 3,343,252 A | 9/1967 | Reesor |
| 3,353,599 A | 11/1967 | Swift |
| 3,354,955 A | 11/1967 | Berry |
| 3,358,760 A | 12/1967 | Blagg |
| 3,358,769 A | 12/1967 | Berry |
| 3,364,993 A | 1/1968 | Skipper |
| 3,371,717 A | 3/1968 | Chenoweth |
| 3,397,745 A | 8/1968 | Owens et al. |
| 3,412,565 A | 11/1968 | Lindsey et al. |
| 3,419,080 A | 12/1968 | Lebourg |
| 3,422,902 A | 1/1969 | Bouchillon |
| 3,424,244 A | 1/1969 | Kinley |
| 3,427,707 A | 2/1969 | Nowosadko |
| 3,463,228 A | 8/1969 | Hearn |
| 3,477,506 A | 11/1969 | Malone |
| 3,489,220 A | 1/1970 | Kinley |
| 3,489,437 A | 1/1970 | Duret |
| 3,498,376 A | 3/1970 | Sizer et al. |
| 3,504,515 A | 4/1970 | Reardon |
| 3,508,771 A | 4/1970 | Duret |
| 3,520,049 A | 7/1970 | Lysenko et al. |
| 3,528,498 A | 9/1970 | Carothers |
| 3,532,174 A | 10/1970 | Diamantides et al. |
| 3,568,773 A | 3/1971 | Chancellor |
| 3,572,777 A | 3/1971 | Blose et al. |
| 3,574,357 A | 4/1971 | Alexandru et al. |
| 3,578,081 A | 5/1971 | Bodine |
| 3,579,805 A | 5/1971 | Kast |
| 3,581,817 A | 6/1971 | Kammerer, Jr. |
| 3,605,887 A | 9/1971 | Lambie |
| 3,631,926 A | 1/1972 | Young |
| 3,665,591 A | 5/1972 | Kowal |
| 3,667,547 A | 6/1972 | Ahlstone |
| 3,669,190 A | 6/1972 | Sizer et al. |
| 3,678,727 A | 7/1972 | Jackson |
| 3,682,256 A | 8/1972 | Stuart |
| 3,687,196 A | 8/1972 | Mullins |
| 3,691,624 A | 9/1972 | Kinley |
| 3,693,717 A | 9/1972 | Wuenschel |
| 3,704,730 A | 12/1972 | Witzig |
| 3,709,306 A | 1/1973 | Curington |
| 3,711,123 A | 1/1973 | Arnold |
| 3,712,376 A | 1/1973 | Owen et al. |
| 3,746,068 A | 7/1973 | Deckert et al. |
| 3,746,091 A | 7/1973 | Owen et al. |
| 3,746,092 A | 7/1973 | Land |
| 3,764,168 A | 10/1973 | Kisling, III et al. |
| 3,776,307 A | 12/1973 | Young |
| 3,779,025 A | 12/1973 | Godley et al. |
| 3,780,562 A | 12/1973 | Kinley |
| 3,781,966 A | 1/1974 | Lieberman |
| 3,785,193 A | 1/1974 | Kinely et al. |
| 3,797,259 A | 3/1974 | Kammerer, Jr. |
| 3,805,567 A | 4/1974 | Agius-Sincero |
| 3,812,912 A | 5/1974 | Wuenschel |
| 3,818,734 A | 6/1974 | Bateman |
| 3,826,124 A | 7/1974 | Baksay |
| 3,830,294 A | 8/1974 | Swanson |
| 3,830,295 A | 8/1974 | Crowe |
| 3,834,742 A | 9/1974 | McPhillips |
| 3,848,668 A | 11/1974 | Sizer et al. |
| 3,866,954 A | 2/1975 | Slator et al. |
| 3,874,446 A | 4/1975 | Crowe |
| 3,885,298 A | 5/1975 | Pogonowski |
| 3,887,006 A | 6/1975 | Pitts |
| 3,893,718 A | 7/1975 | Powell |
| 3,898,163 A | 8/1975 | Mott |
| 3,915,478 A | 10/1975 | Al et al. |
| 3,915,763 A | 10/1975 | Jennings et al. |

| Patent | Type | Date | Inventor |
|---|---|---|---|
| 3,935,910 | A | 2/1976 | Gaudy et al. |
| 3,942,824 | A | 3/1976 | Sable |
| 3,945,444 | A | 3/1976 | Knudson |
| 3,948,321 | A | 4/1976 | Owen et al. |
| 3,963,076 | A | 6/1976 | Winslow |
| 3,970,336 | A | 7/1976 | O'Sickey et al. |
| 3,977,473 | A | 8/1976 | Page, Jr. |
| 3,989,280 | A | 11/1976 | Schwarz |
| 3,997,193 | A | 12/1976 | Tsuda et al. |
| 3,999,605 | A | 12/1976 | Braddick |
| 4,011,652 | A | 3/1977 | Black |
| 4,018,634 | A | 4/1977 | Fencl |
| 4,019,579 | A | 4/1977 | Thuse |
| 4,026,583 | A | 5/1977 | Gottlieb |
| 4,053,247 | A | 10/1977 | Marsh, Jr. |
| 4,069,573 | A | 1/1978 | Rogers, Jr. et al. |
| 4,076,287 | A | 2/1978 | Bill et al. |
| 4,096,913 | A | 6/1978 | Kenneday et al. |
| 4,098,334 | A | 7/1978 | Crowe |
| 4,099,563 | A | 7/1978 | Hutchinson et al. |
| 4,125,937 | A | 11/1978 | Brown et al. |
| 4,152,821 | A | 5/1979 | Scott |
| 4,168,747 | A | 9/1979 | Youmans |
| 4,190,108 | A | 2/1980 | Webber |
| 4,204,312 | A | 5/1980 | Tooker |
| 4,205,422 | A | 6/1980 | Hardwick |
| 4,226,449 | A | 10/1980 | Cole |
| 4,253,687 | A | 3/1981 | Maples |
| 4,257,155 | A | 3/1981 | Hunter |
| 4,274,665 | A | 6/1981 | Marsh, Jr. |
| RE30,802 | E | 11/1981 | Rogers, Jr. |
| 4,304,428 | A | 12/1981 | Grigorian et al. |
| 4,328,983 | A | 5/1982 | Gibson |
| 4,355,664 | A | 10/1982 | Cook et al. |
| 4,359,889 | A | 11/1982 | Kelly |
| 4,363,358 | A | 12/1982 | Ellis |
| 4,366,971 | A | 1/1983 | Lula |
| 4,368,571 | A | 1/1983 | Cooper, Jr. |
| 4,379,471 | A | 4/1983 | Kuenzel |
| 4,380,347 | A | 4/1983 | Sable |
| 4,384,625 | A | 5/1983 | Roper et al. |
| 4,388,752 | A | 6/1983 | Vinciguerra et al. |
| 4,391,325 | A | 7/1983 | Baker et al. |
| 4,393,931 | A | 7/1983 | Muse et al. |
| 4,396,061 | A | 8/1983 | Tamplen et al. |
| 4,397,484 | A | 8/1983 | Miller |
| 4,401,325 | A | 8/1983 | Tsuchiya et al. |
| 4,402,372 | A | 9/1983 | Cherrington |
| 4,407,681 | A | 10/1983 | Ina et al. |
| 4,411,435 | A | 10/1983 | McStravick |
| 4,413,395 | A | 11/1983 | Garnier |
| 4,413,682 | A | 11/1983 | Callihan et al. |
| 4,420,866 | A | 12/1983 | Mueller |
| 4,421,169 | A | 12/1983 | Dearth et al. |
| 4,422,317 | A | 12/1983 | Mueller |
| 4,422,507 | A | 12/1983 | Reimert |
| 4,423,889 | A | 1/1984 | Weise |
| 4,423,986 | A | 1/1984 | Skogberg |
| 4,424,865 | A | 1/1984 | Payton, Jr. |
| 4,429,741 | A | 2/1984 | Hyland |
| 4,440,233 | A | 4/1984 | Baugh et al. |
| 4,442,586 | A | 4/1984 | Ridenour |
| 4,444,250 | A | 4/1984 | Keithahn et al. |
| 4,449,713 | A | 5/1984 | Ishido et al. |
| 4,458,925 | A | 7/1984 | Raulins et al. |
| 4,462,471 | A | 7/1984 | Hipp |
| 4,467,630 | A | 8/1984 | Kelly |
| 4,468,309 | A | 8/1984 | White |
| 4,469,356 | A | 9/1984 | Duret et al. |
| 4,473,245 | A | 9/1984 | Raulins et al. |
| 4,483,399 | A | 11/1984 | Colgate |
| 4,485,847 | A | 12/1984 | Wentzell |
| 4,491,001 | A | 1/1985 | Yoshida |
| 4,495,073 | A | 1/1985 | Beimgraben |
| 4,501,327 | A | 2/1985 | Retz |
| 4,505,017 | A | 3/1985 | Schukei |
| 4,505,987 | A | 3/1985 | Yamada et al. |
| 4,506,432 | A | 3/1985 | Smith |
| 4,507,019 | A | 3/1985 | Thompson |
| 4,508,129 | A | 4/1985 | Brown |
| 4,508,167 | A | 4/1985 | Weinberg et al. |
| 4,511,289 | A | 4/1985 | Herron |
| 4,513,995 | A | 4/1985 | Niehaus et al. |
| 4,519,456 | A | 5/1985 | Cochran |
| 4,526,232 | A | 7/1985 | Hughson et al. |
| 4,526,839 | A | 7/1985 | Herman et al. |
| 4,527,815 | A | 7/1985 | Frick |
| 4,530,231 | A | 7/1985 | Main |
| 4,531,552 | A | 7/1985 | Kim |
| 4,537,429 | A | 8/1985 | Landriault |
| 4,538,442 | A | 9/1985 | Reed |
| 4,538,840 | A | 9/1985 | DeLange |
| 4,541,655 | A | 9/1985 | Hunter |
| 4,550,782 | A | 11/1985 | Lawson |
| 4,550,937 | A | 11/1985 | Duret |
| 4,553,776 | A | 11/1985 | Dodd |
| 4,573,248 | A | 3/1986 | Hackett |
| 4,576,386 | A | 3/1986 | Benson et al. |
| 4,581,817 | A | 4/1986 | Kelly |
| 4,582,348 | A | 4/1986 | Dearden et al. |
| 4,590,227 | A | 5/1986 | Nakamura et al. |
| 4,590,995 | A | 5/1986 | Evans |
| 4,592,577 | A | 6/1986 | Ayres et al. |
| 4,595,063 | A | 6/1986 | Jennings et al. |
| 4,596,913 | A | 6/1986 | Takechi |
| 4,601,343 | A | 7/1986 | Lindsey, Jr. et al. |
| 4,603,889 | A | 8/1986 | Welsh |
| 4,605,063 | A | 8/1986 | Ross |
| 4,611,662 | A | 9/1986 | Harrington |
| 4,614,233 | A | 9/1986 | Menard |
| 4,629,218 | A | 12/1986 | Dubois |
| 4,629,224 | A | 12/1986 | Lanriault |
| 4,630,849 | A | 12/1986 | Fukui et al. |
| 4,632,944 | A | 12/1986 | Thompson |
| 4,634,317 | A | 1/1987 | Skogberg et al. |
| 4,635,333 | A | 1/1987 | Finch |
| 4,637,436 | A | 1/1987 | Stewart, Jr. et al. |
| 4,646,787 | A | 3/1987 | Rush et al. |
| 4,649,492 | A | 3/1987 | Sinha et al. |
| 4,651,831 | A | 3/1987 | Baugh et al. |
| 4,651,836 | A | 3/1987 | Richards |
| 4,656,779 | A | 4/1987 | Fedeli |
| 4,660,863 | A | 4/1987 | Bailey et al. |
| 4,662,446 | A | 5/1987 | Brisco et al. |
| 4,669,541 | A | 6/1987 | Bissonnette |
| 4,674,572 | A | 6/1987 | Gallus |
| 4,676,563 | A | 6/1987 | Curlett et al. |
| 4,682,797 | A | 7/1987 | Hildner |
| 4,685,191 | A | 8/1987 | Mueller et al. |
| 4,685,834 | A | 8/1987 | Jordan |
| 4,693,498 | A | 9/1987 | Baugh et al. |
| 4,711,474 | A | 12/1987 | Patrick |
| 4,714,117 | A | 12/1987 | Dech |
| 4,730,851 | A | 3/1988 | Watts |
| 4,732,416 | A | 3/1988 | Dearden et al. |
| 4,735,444 | A | 4/1988 | Skipper |
| 4,739,654 | A | 4/1988 | Pilkington et al. |
| 4,739,916 | A | 4/1988 | Ayres et al. |
| 4,754,781 | A | 7/1988 | Putter |
| 4,758,025 | A | 7/1988 | Frick |
| 4,762,344 | A | 8/1988 | Perkins et al. |
| 4,776,394 | A | 10/1988 | Lynde et al. |
| 4,778,088 | A | 10/1988 | Miller |
| 4,779,445 | A | 10/1988 | Rabe |
| 4,793,382 | A | 12/1988 | Szalvay |
| 4,796,668 | A | 1/1989 | Depret |

| | | | | | |
|---|---|---|---|---|---|
| 4,799,544 A | 1/1989 | Curlett | 5,156,223 A | 10/1992 | Hipp |
| 4,817,710 A | 4/1989 | Edwards et al. | 5,174,340 A | 12/1992 | Peterson et al. |
| 4,817,712 A | 4/1989 | Bodine | 5,174,376 A | 12/1992 | Singeetham |
| 4,817,716 A | 4/1989 | Taylor et al. | 5,181,571 A | 1/1993 | Mueller et al. |
| 4,822,081 A | 4/1989 | Blose | 5,195,583 A | 3/1993 | Toon et al. |
| 4,825,674 A | 5/1989 | Tanaka et al. | 5,197,553 A | 3/1993 | Leturno |
| 4,826,347 A | 5/1989 | Baril et al. | 5,209,600 A | 5/1993 | Koster |
| 4,827,594 A | 5/1989 | Cartry et al. | 5,226,492 A | 7/1993 | Solaeche et al. |
| 4,828,033 A | 5/1989 | Frison | 5,242,017 A | 9/1993 | Hailey |
| 4,830,109 A | 5/1989 | Wedel | 5,249,628 A | 10/1993 | Surjaatmadja |
| 4,832,382 A | 5/1989 | Kapgan | 5,253,713 A | 10/1993 | Gregg et al. |
| 4,836,278 A | 6/1989 | Stone et al. | RE34,467 E | 12/1993 | Reeves |
| 4,836,579 A | 6/1989 | Wester et al. | 5,275,242 A | 1/1994 | Payne |
| 4,838,349 A | 6/1989 | Berzin | 5,282,508 A | 2/1994 | Ellingsen et al. |
| 4,842,082 A | 6/1989 | Springer | 5,286,393 A | 2/1994 | Oldiges et al. |
| 4,848,459 A | 7/1989 | Blackwell et al. | 5,306,101 A | 4/1994 | Rockower et al. |
| 4,854,338 A | 8/1989 | Grantham | 5,309,621 A | 5/1994 | O'Donnell et al. |
| 4,856,592 A | 8/1989 | Van Bilderbeek et al. | 5,314,014 A | 5/1994 | Tucker |
| 4,865,127 A | 9/1989 | Koster | 5,314,209 A | 5/1994 | Kuhne |
| 4,871,199 A | 10/1989 | Ridenour et al. | 5,318,122 A | 6/1994 | Murray et al. |
| 4,872,253 A | 10/1989 | Carstensen | 5,318,131 A | 6/1994 | Baker |
| 4,887,646 A | 12/1989 | Groves | 5,325,923 A | 7/1994 | Surjaatmadja et al. |
| 4,888,975 A | 12/1989 | Soward et al. | 5,326,137 A | 7/1994 | Lorenz et al. |
| 4,892,337 A | 1/1990 | Gunderson et al. | 5,327,964 A | 7/1994 | O'Donnell et al. |
| 4,893,658 A | 1/1990 | Kimura et al. | 5,330,850 A | 7/1994 | Suzuki et al. |
| 4,904,136 A | 2/1990 | Matsumoto | 5,332,038 A | 7/1994 | Tapp et al. |
| 4,907,828 A | 3/1990 | Change | 5,332,049 A | 7/1994 | Tew |
| 4,911,237 A | 3/1990 | Melenyzer | 5,333,692 A | 8/1994 | Baugh et al. |
| 4,913,758 A | 4/1990 | Koster | 5,335,736 A | 8/1994 | Windsor |
| 4,915,177 A | 4/1990 | Claycomb | 5,337,808 A | 8/1994 | Graham |
| 4,915,426 A | 4/1990 | Skipper | 5,337,823 A | 8/1994 | Nobileau |
| 4,917,409 A | 4/1990 | Reeves | 5,337,827 A | 8/1994 | Hromas et al. |
| 4,919,989 A | 4/1990 | Colangelo | 5,339,894 A | 8/1994 | Stotler |
| 4,921,045 A | 5/1990 | Richardson | 5,343,949 A | 9/1994 | Ross et al. |
| 4,924,949 A | 5/1990 | Curlett | 5,346,007 A | 9/1994 | Dillon et al. |
| 4,930,573 A | 6/1990 | Lane et al. | 5,348,087 A | 9/1994 | Williamson, Jr. |
| 4,934,038 A | 6/1990 | Caudill | 5,348,093 A | 9/1994 | Wood et al. |
| 4,934,312 A | 6/1990 | Koster et al. | 5,348,095 A | 9/1994 | Worrall et al. |
| 4,938,291 A | 7/1990 | Lynde et al. | 5,348,668 A | 9/1994 | Oldiges et al. |
| 4,941,512 A | 7/1990 | McParland | 5,351,752 A | 10/1994 | Wood et al. |
| 4,941,532 A | 7/1990 | Hurt et al. | 5,360,239 A | 11/1994 | Klementich |
| 4,942,925 A | 7/1990 | Themig | 5,360,292 A | 11/1994 | Allen et al. |
| 4,942,926 A | 7/1990 | Lessi | 5,361,836 A | 11/1994 | Sorem et al. |
| 4,958,691 A | 9/1990 | Hipp | 5,361,843 A | 11/1994 | Shy et al. |
| 4,968,184 A | 11/1990 | Reid | 5,366,010 A | 11/1994 | Zwart |
| 4,971,152 A | 11/1990 | Koster et al. | 5,366,012 A | 11/1994 | Lohbeck |
| 4,976,322 A | 12/1990 | Abdrakhmanov et al. | 5,368,075 A | 11/1994 | Bäro et al. |
| 4,981,250 A | 1/1991 | Persson | 5,370,425 A | 12/1994 | Dougherty et al. |
| 4,995,464 A | 2/1991 | Watkins et al. | 5,375,661 A | 12/1994 | Daneshy et al. |
| 5,014,779 A | 5/1991 | Meling et al. | 5,388,648 A | 2/1995 | Jordan, Jr. |
| 5,015,017 A | 5/1991 | Geary | 5,390,735 A | 2/1995 | Williamson, Jr. |
| 5,026,074 A | 6/1991 | Hoes et al. | 5,390,742 A | 2/1995 | Dines et al. |
| 5,031,370 A | 7/1991 | Jewett | 5,396,957 A | 3/1995 | Surjaatmadja et al. |
| 5,031,699 A | 7/1991 | Artynov et al. | 5,400,827 A | 3/1995 | Baro et al. |
| 5,040,283 A | 8/1991 | Pelgrom | 5,405,171 A | 4/1995 | Allen et al. |
| 5,044,676 A | 9/1991 | Burton et al. | 5,411,301 A | 5/1995 | Moyer et al. |
| 5,048,871 A | 9/1991 | Pfeiffer et al. | 5,413,180 A | 5/1995 | Ross et al. |
| 5,052,483 A | 10/1991 | Hudson | 5,419,595 A | 5/1995 | Yamamoto et al. |
| 5,059,043 A | 10/1991 | Kuhne | 5,425,559 A | 6/1995 | Nobileau |
| 5,064,004 A | 11/1991 | Lundel | 5,426,130 A | 6/1995 | Thurder et al. |
| 5,079,837 A | 1/1992 | Vanselow | 5,431,831 A | 7/1995 | Vincent |
| 5,083,608 A | 1/1992 | Abdrakhmanov et al. | 5,435,395 A | 7/1995 | Connell |
| 5,093,015 A | 3/1992 | Oldiges | 5,439,320 A | 8/1995 | Abrams |
| 5,095,991 A | 3/1992 | Milberger | 5,443,129 A | 8/1995 | Bailey et al. |
| 5,097,710 A | 3/1992 | Palynchuk | 5,447,201 A | 9/1995 | Mohn |
| 5,101,653 A | 4/1992 | Hermes et al. | 5,454,419 A | 10/1995 | Vloedman |
| 5,105,888 A | 4/1992 | Pollock et al. | 5,456,319 A | 10/1995 | Schmidt et al. |
| 5,107,221 A | 4/1992 | N'Guyen et al. | 5,458,194 A | 10/1995 | Brooks |
| 5,119,661 A | 6/1992 | Abdrakhmanov et al. | 5,462,120 A | 10/1995 | Gondouin |
| 5,134,891 A | 8/1992 | Canevet | 5,467,822 A | 11/1995 | Zwart |
| 5,150,755 A | 9/1992 | Cassel et al. | 5,472,055 A | 12/1995 | Simson et al. |
| 5,156,043 A | 10/1992 | Ose | 5,474,334 A | 12/1995 | Eppink |
| 5,156,213 A | 10/1992 | George et al. | 5,492,173 A | 2/1996 | Kilgore et al. |

| | | | | | | |
|---|---|---|---|---|---|---|
| 5,494,106 | A | 2/1996 | Gueguen et al. | 6,012,523 A | 1/2000 | Campbell et al. |
| 5,507,343 | A | 4/1996 | Carlton et al. | 6,012,874 A | 1/2000 | Groneck et al. |
| 5,511,620 | A | 4/1996 | Baugh et al. | 6,015,012 A | 1/2000 | Reddick |
| 5,524,937 | A | 6/1996 | Sides, III et al. | 6,017,168 A | 1/2000 | Fraser et al. |
| 5,535,824 | A | 7/1996 | Hudson | 6,021,850 A | 2/2000 | Woo et al. |
| 5,536,422 | A | 7/1996 | Oldiges et al. | 6,027,145 A | 2/2000 | Tsuru et al. |
| 5,540,281 | A | 7/1996 | Round | 6,029,748 A | 2/2000 | Forsyth et al. |
| 5,554,244 | A | 9/1996 | Ruggles et al. | 6,035,954 A | 3/2000 | Hipp |
| 5,566,772 | A | 10/1996 | Coone et al. | 6,044,906 A | 4/2000 | Saltel |
| 5,567,335 | A | 10/1996 | Baessler et al. | 6,047,505 A | 4/2000 | Willow |
| 5,576,485 | A | 11/1996 | Serata | 6,047,774 A | 4/2000 | Allen |
| 5,584,512 | A | 12/1996 | Carstensen | 6,050,341 A | 4/2000 | Metcalf |
| 5,606,792 | A | 3/1997 | Schafer | 6,050,346 A | 4/2000 | Hipp |
| 5,611,399 | A | 3/1997 | Richard et al. | 6,056,059 A | 5/2000 | Ohmer |
| 5,613,557 | A | 3/1997 | Blount et al. | 6,056,324 A | 5/2000 | Reimert et al. |
| 5,617,918 | A | 4/1997 | Cooksey et al. | 6,062,324 A | 5/2000 | Hipp |
| 5,642,560 | A | 7/1997 | Tabuchi et al. | 6,065,500 A | 5/2000 | Metcalfe |
| 5,642,781 | A | 7/1997 | Richard | 6,070,671 A | 6/2000 | Cumming et al. |
| 5,662,180 | A | 9/1997 | Coffman et al. | 6,073,332 A | 6/2000 | Turner |
| 5,664,327 | A | 9/1997 | Swars | 6,073,692 A | 6/2000 | Wood et al. |
| 5,667,011 | A | 9/1997 | Gill et al. | 6,073,698 A | 6/2000 | Shultz et al. |
| 5,667,252 | A | 9/1997 | Schafer et al. | 6,074,133 A | 6/2000 | Kelsey |
| 5,678,609 | A | 10/1997 | Washburn | 6,078,031 A | 6/2000 | Bliault et al. |
| 5,685,369 | A | 11/1997 | Ellis et al. | 6,079,495 A | 6/2000 | Ohmer |
| 5,689,871 | A | 11/1997 | Carstensen | 6,085,838 A | 7/2000 | Vercaemer et al. |
| 5,695,008 | A | 12/1997 | Bertet et al. | 6,089,320 A | 7/2000 | LaGrange |
| 5,695,009 | A | 12/1997 | Hipp | 6,098,717 A | 8/2000 | Bailey et al. |
| 5,697,442 | A | 12/1997 | Baldridge | 6,102,119 A | 8/2000 | Raines |
| 5,697,449 | A | 12/1997 | Hennig et al. | 6,109,355 A | 8/2000 | Reid |
| 5,718,288 | A | 2/1998 | Bertet et al. | 6,112,818 A | 9/2000 | Campbell |
| 5,738,146 | A | 4/1998 | Abe | 6,131,265 A | 10/2000 | Bird |
| 5,743,335 | A | 4/1998 | Bussear | 6,135,208 A | 10/2000 | Gano et al. |
| 5,749,419 | A | 5/1998 | Coronado et al. | 6,138,761 A | 10/2000 | Freeman et al. |
| 5,749,585 | A | 5/1998 | Lembcke | 6,142,230 A | 11/2000 | Smalley et al. |
| 5,755,895 | A | 5/1998 | Tamehiro et al. | 6,155,613 A | 12/2000 | Quadflieg et al. |
| 5,775,422 | A | 7/1998 | Wong et al. | 6,158,785 A | 12/2000 | Beaulier et al. |
| 5,785,120 | A | 7/1998 | Smalley et al. | 6,158,963 A | 12/2000 | Hollis |
| 5,787,933 | A | 8/1998 | Russ et al. | 6,167,970 B1 | 1/2001 | Stout |
| 5,791,419 | A | 8/1998 | Valisalo | 6,182,775 B1 | 2/2001 | Hipp |
| 5,794,702 | A | 8/1998 | Nobileau | 6,196,336 B1 | 3/2001 | Fincher et al. |
| 5,794,840 | A * | 8/1998 | Hohl et al. ............ 228/151 | 6,220,306 B1 | 4/2001 | Omura et al. |
| 5,797,454 | A | 8/1998 | Hipp | 6,226,855 B1 | 5/2001 | Maine |
| 5,829,520 | A | 11/1998 | Johnson | 6,231,086 B1 | 5/2001 | Tierling |
| 5,829,524 | A | 11/1998 | Flanders et al. | 6,237,967 B1 | 5/2001 | Yamamoto et al. |
| 5,829,797 | A | 11/1998 | Yamamoto et al. | 6,250,385 B1 | 6/2001 | Montaron |
| 5,833,001 | A | 11/1998 | Song et al. | 6,253,846 B1 | 7/2001 | Nazzai et al. |
| 5,845,945 | A | 12/1998 | Carstensen | 6,253,850 B1 | 7/2001 | Nazzai et al. |
| 5,849,188 | A | 12/1998 | Voll et al. | 6,263,966 B1 | 7/2001 | Haut et al. |
| 5,857,524 | A | 1/1999 | Harris | 6,263,968 B1 | 7/2001 | Freeman et al. |
| 5,862,866 | A | 1/1999 | Springer | 6,263,972 B1 | 7/2001 | Richard et al. |
| 5,875,851 | A | 3/1999 | Vick, Jr. et al. | 6,267,181 B1 | 7/2001 | Rhein-Knudsen et al. |
| 5,885,941 | A | 3/1999 | Sateva et al. | 6,273,634 B1 | 8/2001 | Lohbeck |
| 5,895,079 | A | 4/1999 | Carstensen et al. | 6,275,556 B1 | 8/2001 | Kinney et al. |
| 5,901,789 | A | 5/1999 | Donnelly et al. | 6,283,211 B1 | 9/2001 | Vloedman |
| 5,918,677 | A | 7/1999 | Head | 6,286,558 B1 | 9/2001 | Quigley et al. |
| 5,924,745 | A | 7/1999 | Campbell | 6,302,211 B1 | 10/2001 | Nelson et al. |
| 5,931,511 | A | 8/1999 | DeLange et al. | 6,311,792 B1 | 11/2001 | Scott et al. |
| 5,933,945 | A | 8/1999 | Thomeer et al. | 6,315,040 B1 | 11/2001 | Donnelly |
| 5,944,100 | A | 8/1999 | Hipp | 6,315,043 B1 | 11/2001 | Farrant et al. |
| 5,944,107 | A | 8/1999 | Ohmer | 6,318,457 B1 | 11/2001 | Den Boer et al. |
| 5,944,108 | A | 8/1999 | Baugh et al. | 6,318,465 B1 | 11/2001 | Coon et al. |
| 5,951,207 | A | 9/1999 | Chen | 6,322,109 B1 | 11/2001 | Campbell et al. |
| 5,957,195 | A | 9/1999 | Bailey et al. | 6,325,148 B1 | 12/2001 | Trahan et al. |
| 5,964,288 | A | 10/1999 | Leighton et al. | 6,328,113 B1 | 12/2001 | Cook |
| 5,971,443 | A | 10/1999 | Noel et al. | 6,334,351 B1 | 1/2002 | Tsuchiya |
| 5,975,587 | A | 11/1999 | Wood et al. | 6,343,495 B1 | 2/2002 | Cheppe et al. |
| 5,979,560 | A | 11/1999 | Nobileau | 6,343,657 B1 | 2/2002 | Baugh et al. |
| 5,984,369 | A | 11/1999 | Crook et al. | 6,345,373 B1 | 2/2002 | Chakradhar et al. |
| 5,984,568 | A | 11/1999 | Lohbeck | 6,345,431 B1 | 2/2002 | Greig |
| 5,985,053 | A * | 11/1999 | Hara et al. ............ 148/335 | 6,352,112 B1 | 3/2002 | Mills |
| 6,009,611 | A | 1/2000 | Adams et al. | 6,354,373 B1 | 3/2002 | Vercaemer et al. |
| 6,012,521 | A | 1/2000 | Zunkel et al. | 6,390,720 B1 | 5/2002 | LeBegue et al. |
| 6,012,522 | A | 1/2000 | Donnelly et al. | 6,405,761 B1 | 6/2002 | Shimizu et al. |

| | | | | | | |
|---|---|---|---|---|---|---|
| 6,406,063 B1 | 6/2002 | Pfeiffer | 6,708,767 B2 | 3/2004 | Harrall et al. | |
| 6,409,175 B1 | 6/2002 | Evans et al. | 6,712,154 B2 | 3/2004 | Cook et al. | |
| 6,419,025 B1 | 7/2002 | Lohbeck et al. | 6,712,401 B2 | 3/2004 | Coulon et al. | |
| 6,419,026 B1 | 7/2002 | MacKenzie et al. | 6,719,064 B2 | 4/2004 | Price-Smith et al. | |
| 6,419,033 B1 | 7/2002 | Hahn et al. | 6,722,427 B2 | 4/2004 | Gano et al. | |
| 6,419,147 B1 | 7/2002 | Daniel | 6,722,437 B2 | 4/2004 | Vercaemer et al. | |
| 6,425,444 B1 | 7/2002 | Metcalfe et al. | 6,722,443 B1 | 4/2004 | Metcalfe | |
| 6,431,277 B1 | 8/2002 | Cox et al. | 6,725,917 B2 | 4/2004 | Metcalfe | |
| 6,443,247 B1 | 9/2002 | Wardley | 6,725,919 B2 | 4/2004 | Cook et al. | |
| 6,446,724 B2 | 9/2002 | Baugh et al. | 6,725,934 B2 | 4/2004 | Coronado et al. | |
| 6,447,025 B1 | 9/2002 | Smith | 6,725,939 B2 | 4/2004 | Richard | |
| 6,450,261 B1 | 9/2002 | Baugh | 6,732,806 B2 | 5/2004 | Mauldin et al. | |
| 6,454,013 B1 | 9/2002 | Metcalfe | 6,739,392 B2 | 5/2004 | Cook et al. | |
| 6,454,024 B1 | 9/2002 | Nackerud | 6,745,845 B2 | 6/2004 | Cook et al. | |
| 6,457,532 B1 | 10/2002 | Simpson | 6,749,954 B2 * | 6/2004 | Toyooka et al. | 428/683 |
| 6,457,533 B1 | 10/2002 | Metcalfe | 6,755,447 B2 | 6/2004 | Galle, Jr. et al. | |
| 6,457,749 B1 | 10/2002 | Heijnen | 6,758,278 B2 | 7/2004 | Cook et al. | |
| 6,460,615 B1 | 10/2002 | Heijnen | 6,772,841 B2 | 8/2004 | Gano | |
| 6,464,008 B1 | 10/2002 | Roddy et al. | 6,796,380 B2 | 9/2004 | Xu | |
| 6,464,014 B1 | 10/2002 | Bernat | 6,814,147 B2 | 11/2004 | Baugh | |
| 6,470,966 B2 | 10/2002 | Cook et al. | 6,817,633 B2 | 11/2004 | Brill et al. | |
| 6,478,092 B2 | 11/2002 | Voll et al. | 6,820,690 B2 | 11/2004 | Vercaemer et al. | |
| 6,491,108 B1 | 12/2002 | Slup et al. | 6,823,937 B1 | 11/2004 | Cook et al. | |
| 6,497,289 B1 | 12/2002 | Cook et al. | 6,832,649 B2 | 12/2004 | Bode et al. | |
| 6,516,887 B2 | 2/2003 | Nguyen et al. | 6,834,725 B2 | 12/2004 | Whanger et al. | |
| 6,517,126 B1 | 2/2003 | Peterson et al. | 6,843,322 B2 | 1/2005 | Burtner et al. | |
| 6,527,049 B2 | 3/2003 | Metcalfe et al. | 6,857,473 B2 | 2/2005 | Cook et al. | |
| 6,543,545 B1 | 4/2003 | Chatterji et al. | 6,880,632 B2 | 4/2005 | Tom et al. | |
| 6,543,552 B1 | 4/2003 | Metcalfe et al. | 6,892,819 B2 | 5/2005 | Cook et al. | |
| 6,550,539 B2 | 4/2003 | Maguire et al. | 6,902,000 B2 | 6/2005 | Simpson et al. | |
| 6,550,821 B2 | 4/2003 | DeLange et al. | 6,902,652 B2 | 6/2005 | Heijnen | |
| 6,557,640 B1 | 5/2003 | Cook et al. | 6,923,261 B2 | 8/2005 | Metcalfe et al. | |
| 6,557,906 B1 | 5/2003 | Carcagno | 6,935,429 B2 | 8/2005 | Badrack | |
| 6,561,227 B2 | 5/2003 | Cook et al. | 6,935,430 B2 | 8/2005 | Harreil et al. | |
| 6,561,279 B2 | 5/2003 | MacKenzie et al. | 6,966,370 B2 | 11/2005 | Cook et al. | |
| 6,564,875 B1 | 5/2003 | Bullock | 6,976,539 B2 | 12/2005 | Metcalfe et al. | |
| 6,568,471 B1 | 5/2003 | Cook et al. | 6,976,541 B2 | 12/2005 | Brisco et al. | |
| 6,568,488 B2 | 5/2003 | Wentworth et al. | 7,000,953 B2 | 2/2006 | Berghaus | |
| 6,575,240 B1 | 6/2003 | Cook et al. | 7,007,760 B2 | 3/2006 | Lohbeck | |
| 6,578,630 B2 | 6/2003 | Simpson et al. | 7,021,390 B2 | 4/2006 | Cook et al. | |
| 6,585,053 B2 | 7/2003 | Coon | 7,036,582 B2 | 5/2006 | Cook et al. | |
| 6,585,299 B1 | 7/2003 | Quadflieg et al. | 7,077,211 B2 | 7/2006 | Cook et al. | |
| 6,591,905 B2 | 7/2003 | Coon | 7,077,213 B2 | 7/2006 | Cook et al. | |
| 6,598,677 B1 | 7/2003 | Baugh et al. | 7,086,475 B2 | 8/2006 | Cook | |
| 6,598,678 B1 | 7/2003 | Simpson | 7,100,685 B2 | 9/2006 | Cook et al. | |
| 6,604,763 B1 | 8/2003 | Cook et al. | 7,121,337 B2 | 10/2006 | Cook et al. | |
| 6,607,220 B2 | 8/2003 | Sivley, IV | 7,121,352 B2 | 10/2006 | Cook et al. | |
| 6,609,735 B1 | 8/2003 | DeLange et al. | 2001/0002626 A1 * | 6/2001 | Frank et al. | 175/57 |
| 6,619,696 B2 | 9/2003 | Baugh et al. | 2001/0020532 A1 | 9/2001 | Baugh et al. | |
| 6,622,797 B2 | 9/2003 | Sivley, IV | 2001/0045284 A1 | 11/2001 | Simpson et al. | |
| 6,629,567 B2 | 10/2003 | Lauritzen et al. | 2001/0045289 A1 | 11/2001 | Cook et al. | |
| 6,631,759 B2 | 10/2003 | Cook et al. | 2001/0047870 A1 | 12/2001 | Cook et al. | |
| 6,631,760 B2 | 10/2003 | Cook et al. | 2002/0011339 A1 | 1/2002 | Murray | |
| 6,631,765 B2 | 10/2003 | Baugh et al. | 2002/0014339 A1 | 2/2002 | Ross | |
| 6,631,769 B2 | 10/2003 | Cook et al. | 2002/0020524 A1 | 2/2002 | Gano | |
| 6,634,431 B2 | 10/2003 | Cook et al. | 2002/0020531 A1 | 2/2002 | Ohmer | |
| 6,640,895 B2 | 11/2003 | Murray | 2002/0033261 A1 | 3/2002 | Metcalfe | |
| 6,640,903 B1 | 11/2003 | Cook et al. | 2002/0060068 A1 | 5/2002 | Cook et al. | |
| 6,648,075 B2 | 11/2003 | Badrak et al. | 2002/0062956 A1 | 5/2002 | Murray et al. | |
| 6,659,509 B2 | 12/2003 | Goto et al. | 2002/0066576 A1 | 6/2002 | Cook et al. | |
| 6,662,876 B2 | 12/2003 | Lauritzen | 2002/0066578 A1 | 6/2002 | Broome | |
| 6,668,937 B1 | 12/2003 | Murray | 2002/0070023 A1 | 6/2002 | Turner et al. | |
| 6,672,759 B2 | 1/2004 | Feger | 2002/0070031 A1 | 6/2002 | Voll et al. | |
| 6,679,328 B2 | 1/2004 | Davis et al. | 2002/0079101 A1 | 6/2002 | Baugh et al. | |
| 6,681,862 B2 | 1/2004 | Freeman | 2002/0084070 A1 | 7/2002 | Voll et al. | |
| 6,684,947 B2 | 2/2004 | Cook et al. | 2002/0092654 A1 | 7/2002 | Coronado et al. | |
| 6,688,397 B2 | 2/2004 | McClurkin et al. | 2002/0108756 A1 | 8/2002 | Harrall et al. | |
| 6,695,012 B1 | 2/2004 | Ring et al. | 2002/0139540 A1 | 10/2002 | Lauritzen | |
| 6,695,065 B2 | 2/2004 | Simpson et al. | 2002/0144822 A1 | 10/2002 | Hackworth et al. | |
| 6,698,517 B2 | 3/2004 | Simpson | 2002/0148612 A1 | 10/2002 | Cook et al. | |
| 6,701,598 B2 | 3/2004 | Chen et al. | 2002/0185274 A1 | 12/2002 | Simpson et al. | |
| 6,702,030 B2 | 3/2004 | Simpson | 2002/0189816 A1 | 12/2002 | Cook et al. | |
| 6,705,395 B2 | 3/2004 | Cook et al. | 2002/0195252 A1 | 12/2002 | Maguire et al. | |

| | | |
|---|---|---|
| 2002/0195256 A1 | 12/2002 | Metcalfe et al. |
| 2003/0024708 A1 | 2/2003 | Ring et al. |
| 2003/0024711 A1 | 2/2003 | Simpson et al. |
| 2003/0034177 A1 | 2/2003 | Chitwood et al. |
| 2003/0042022 A1 | 3/2003 | Lauritzen et al. |
| 2003/0047322 A1 | 3/2003 | Maguire et al. |
| 2003/0047323 A1 | 3/2003 | Jackson et al. |
| 2003/0056991 A1 | 3/2003 | Hahn et al. |
| 2003/0066655 A1 | 4/2003 | Cook et al. |
| 2003/0067166 A1 | 4/2003 | Sivley, IV |
| 2003/0075338 A1 | 4/2003 | Sivley, IV |
| 2003/0075339 A1 | 4/2003 | Gano et al. |
| 2003/0094277 A1 | 5/2003 | Cook et al. |
| 2003/0094278 A1 | 5/2003 | Cook et al. |
| 2003/0094279 A1 | 5/2003 | Ring et al. |
| 2003/0098154 A1 | 5/2003 | Cook et al. |
| 2003/0098162 A1 | 5/2003 | Cook |
| 2003/0107217 A1 | 6/2003 | Daigle et al. |
| 2003/0111234 A1 | 6/2003 | McClurkin et al. |
| 2003/0116318 A1 | 6/2003 | Metcalfe |
| 2003/0116325 A1 | 6/2003 | Cook et al. |
| 2003/0121558 A1 | 7/2003 | Cook et al. |
| 2003/0121655 A1 | 7/2003 | Lauritzen et al. |
| 2003/0121669 A1 | 7/2003 | Cook et al. |
| 2003/0140673 A1 | 7/2003 | Marr et al. |
| 2003/0150608 A1 | 8/2003 | Smith, Jr. et al. |
| 2003/0168222 A1 | 9/2003 | Maguire et al. |
| 2003/0173090 A1 | 9/2003 | Cook et al. |
| 2003/0192705 A1 | 10/2003 | Cook et al. |
| 2003/0221841 A1 | 12/2003 | Burtner et al. |
| 2003/0222455 A1 | 12/2003 | Cook et al. |
| 2004/0011534 A1 | 1/2004 | Simonds et al. |
| 2004/0045616 A1 | 3/2004 | Cook et al. |
| 2004/0045718 A1 | 3/2004 | Brisco et al. |
| 2004/0060706 A1 | 4/2004 | Stephenson |
| 2004/0065446 A1 | 4/2004 | Tran et al. |
| 2004/0069499 A1 | 4/2004 | Cook et al. |
| 2004/0112589 A1 | 6/2004 | Cook et al. |
| 2004/0112606 A1 | 6/2004 | Lewis et al. |
| 2004/0118574 A1 | 6/2004 | Cook et al. |
| 2004/0123983 A1 | 7/2004 | Cook et al. |
| 2004/0123988 A1 | 7/2004 | Cook et al. |
| 2004/0129431 A1 | 7/2004 | Jackson |
| 2004/0149431 A1 | 8/2004 | Wylie et al. |
| 2004/0159446 A1 | 8/2004 | Haugen et al. |
| 2004/0188099 A1 | 9/2004 | Cook et al. |
| 2004/0194966 A1 | 10/2004 | Zimmerman |
| 2004/0216873 A1 | 11/2004 | Frost, Jr. et al. |
| 2004/0221996 A1 | 11/2004 | Burge |
| 2004/0231839 A1 | 11/2004 | Ellington et al. |
| 2004/0231855 A1 | 11/2004 | Cook et al. |
| 2004/0238181 A1 | 12/2004 | Cook et al. |
| 2004/0244968 A1 | 12/2004 | Cook et al. |
| 2004/0262014 A1 | 12/2004 | Cook et al. |
| 2005/0011641 A1 | 1/2005 | Cook et al. |
| 2005/0015963 A1 | 1/2005 | Costa et al. |
| 2005/0028988 A1 | 2/2005 | Cook et al. |
| 2005/0039910 A1 | 2/2005 | Lohbeck |
| 2005/0039928 A1 | 2/2005 | Cook et al. |
| 2005/0045324 A1 | 3/2005 | Cook et al. |
| 2005/0045341 A1 | 3/2005 | Cook et al. |
| 2005/0045342 A1 | 3/2005 | Luke et al. |
| 2005/0056433 A1 | 3/2005 | Watson et al. |
| 2005/0077051 A1 | 4/2005 | Cook et al. |
| 2005/0081358 A1 | 4/2005 | Cook et al. |
| 2005/0087337 A1 | 4/2005 | Brisco et al. |
| 2005/0098323 A1 | 5/2005 | Cook et al. |
| 2005/0103502 A1 | 5/2005 | Watson et al. |
| 2005/0123639 A1 | 6/2005 | Ring et al. |
| 2005/0133225 A1 | 6/2005 | Oosterling |
| 2005/0138790 A1 | 6/2005 | Cook et al. |
| 2005/0144771 A1 | 7/2005 | Cook et al. |
| 2005/0144772 A1 | 7/2005 | Cook et al. |
| 2005/0144777 A1 | 7/2005 | Cook et al. |
| 2005/0150098 A1 | 7/2005 | Cook et al. |
| 2005/0150660 A1 | 7/2005 | Cook et al. |
| 2005/0161228 A1 | 7/2005 | Cook et al. |
| 2005/0166387 A1 | 8/2005 | Cook et al. |
| 2005/0166388 A1 | 8/2005 | Cook et al. |
| 2005/0172473 A1 | 8/2005 | Cook et al. |
| 2005/0173108 A1 | 8/2005 | Cook et al. |
| 2005/0183863 A1 | 8/2005 | Cook et al. |
| 2005/0205253 A1 | 9/2005 | Cook et al. |
| 2005/0217768 A1 | 10/2005 | Asahi et al. |
| 2005/0217865 A1 | 10/2005 | Ring et al. |
| 2005/0217866 A1 | 10/2005 | Watson et al. |
| 2005/0223535 A1 | 10/2005 | Cook et al. |
| 2005/0224225 A1 | 10/2005 | Cook et al. |
| 2005/0230102 A1 | 10/2005 | Cook et al. |
| 2005/0230103 A1 | 10/2005 | Cook et al. |
| 2005/0230104 A1 | 10/2005 | Cook et al. |
| 2005/0236163 A1 | 10/2005 | Cook et al. |
| 2005/0244578 A1 | 11/2005 | Van Egmond et al. |
| 2005/0246883 A1 | 11/2005 | Alliot et al. |
| 2005/0247453 A1 | 11/2005 | Shuster et al. |
| 2005/0265788 A1 | 12/2005 | Renkema |
| 2005/0269107 A1 | 12/2005 | Cook et al. |
| 2006/0027371 A1 | 2/2006 | Gorrara |
| 2006/0032640 A1 | 2/2006 | Costa et al. |
| 2006/0048948 A1 | 3/2006 | Noel |
| 2006/0054330 A1 | 3/2006 | Ring et al. |
| 2006/0065403 A1 | 3/2006 | Watson et al. |
| 2006/0065406 A1 | 3/2006 | Shuster et al. |
| 2006/0096762 A1 | 5/2006 | Brisco |
| 2006/0102360 A1 | 5/2006 | Brisco et al. |
| 2006/0112768 A1 | 6/2006 | Shuster et al. |
| 2006/0113086 A1 | 6/2006 | Costa et al. |

FOREIGN PATENT DOCUMENTS

| | | |
|---|---|---|
| AU | 773168 | 5/2004 |
| AU | 770008 | 7/2004 |
| AU | 770359 | 7/2004 |
| AU | 771884 | 8/2004 |
| AU | 776580 | 1/2005 |
| AU | 780123 | 3/2005 |
| AU | 2001269810 | 8/2005 |
| AU | 782901 | 9/2005 |
| AU | 783245 | 10/2005 |
| AU | 2001294802 | 10/2005 |
| AU | 2001283026 | 7/2006 |
| AU | 2002239857 | 8/2006 |
| CA | 736288 | 6/1966 |
| CA | 771462 | 11/1967 |
| CA | 1171310 | 7/1984 |
| CA | 2292171 | 6/2000 |
| CA | 2298139 | 8/2000 |
| CA | 2234386 | 3/2003 |
| CA | 2414449 | 9/2006 |
| DE | 174521 | 4/1953 |
| DE | 2458188 | 6/1975 |
| DE | 203767 | 11/1983 |
| DE | 233607 A1 | 3/1986 |
| DE | 278517 A1 | 5/1990 |
| EP | 0084940 A1 | 8/1983 |
| EP | 0272511 | 12/1987 |
| EP | 0294264 | 5/1988 |
| EP | 0553566 A1 | 12/1992 |
| EP | 0633391 A2 | 1/1995 |
| EP | 0713953 B1 | 11/1995 |
| EP | 0823534 | 2/1998 |
| EP | 0881354 | 12/1998 |
| EP | 0881359 | 12/1998 |
| EP | 0899420 | 3/1999 |
| EP | 0937861 | 8/1999 |
| EP | 0952305 | 10/1999 |

| | | | | | | |
|---|---|---|---|---|---|---|
| EP | 0952306 | | 10/1999 | GB | 2380214 B | 8/2003 |
| EP | 1141515 | A | 10/2001 | GB | 2380215 B | 8/2003 |
| EP | 1152120 | A2 | 11/2001 | GB | 2348223 B | 9/2003 |
| EP | 1152120 | A3 | 11/2001 | GB | 2347952 B | 10/2003 |
| EP | 1235972 | A | 9/2002 | GB | 2348657 B | 10/2003 |
| EP | 1555386 | A1 | 7/2005 | GB | 2364802 B | 10/2003 |
| FR | 1325596 | | 6/1962 | GB | 2384800 B | 10/2003 |
| FR | 2717855 | A1 | 9/1995 | GB | 2384801 B | 10/2003 |
| FR | 2741907 | A1 | 6/1997 | GB | 2384803 B | 10/2003 |
| FR | 2771133 | A | 5/1999 | GB | 2384804 B | 10/2003 |
| FR | 2780751 | | 1/2000 | GB | 2384805 B | 10/2003 |
| FR | 2841626 | A1 | 1/2004 | GB | 2384806 B | 10/2003 |
| GB | 557823 | | 12/1943 | GB | 2384807 B | 10/2003 |
| GB | 788150 | | 12/1957 | GB | 2384808 B | 10/2003 |
| GB | 851096 | | 10/1960 | GB | 2385353 B | 10/2003 |
| GB | 961750 | | 6/1964 | GB | 2385354 B | 10/2003 |
| GB | 1000383 | | 10/1965 | GB | 2385355 B | 10/2003 |
| GB | 1062610 | | 3/1967 | GB | 2385356 B | 10/2003 |
| GB | 1111536 | | 5/1968 | GB | 2385357 B | 10/2003 |
| GB | 1448304 | | 9/1976 | GB | 2385358 B | 10/2003 |
| GB | 1460864 | | 1/1977 | GB | 2385359 B | 10/2003 |
| GB | 1542847 | | 3/1979 | GB | 2385360 B | 10/2003 |
| GB | 1563740 | | 3/1980 | GB | 2385361 B | 10/2003 |
| GB | 2058877 | A | 4/1981 | GB | 2385362 B | 10/2003 |
| GB | 2108228 | A | 5/1983 | GB | 2385363 B | 10/2003 |
| GB | 2115860 | A | 9/1983 | GB | 2385619 B | 10/2003 |
| GB | 2125876 | A | 3/1984 | GB | 2385620 B | 10/2003 |
| GB | 2211573 | A | 7/1989 | GB | 2385621 B | 10/2003 |
| GB | 2216926 | A | 10/1989 | GB | 2385622 B | 10/2003 |
| GB | 2243191 | A | 10/1991 | GB | 2385623 B | 10/2003 |
| GB | 2256910 | A | 12/1992 | GB | 2387405 A | 10/2003 |
| GB | 2257184 | A | 6/1993 | GB | 2387861 A | 10/2003 |
| GB | 2305682 | A | 4/1997 | GB | 2388134 A | 11/2003 |
| GB | 2325949 | A | 5/1998 | GB | 2388860 A | 11/2003 |
| GB | 2322655 | A | 9/1998 | GB | 2355738 B | 12/2003 |
| GB | 2326896 | A | 1/1999 | GB | 2374622 B | 12/2003 |
| GB | 2329916 | A | 4/1999 | GB | 2388391 B | 12/2003 |
| GB | 2329918 | A | 4/1999 | GB | 2388392 B | 12/2003 |
| GB | 2338383 | A | 10/1999 | GB | 2388393 B | 12/2003 |
| GB | 2355738 | A | 4/2000 | GB | 2388394 B | 12/2003 |
| GB | 2343691 | A | 5/2000 | GB | 2388395 B | 12/2003 |
| GB | 2344606 | A | 6/2000 | GB | 2356651 B | 2/2004 |
| GB | 2368865 | A | 7/2000 | GB | 2368865 B | 2/2004 |
| GB | 2346165 | A | 8/2000 | GB | 2388860 B | 2/2004 |
| GB | 2348632 | A | 8/2000 | GB | 2388861 B | 2/2004 |
| GB | 2347445 | A | 9/2000 | GB | 2388862 B | 2/2004 |
| GB | 2347446 | A | 9/2000 | GB | 2391886 A | 2/2004 |
| GB | 2347950 | A | 9/2000 | GB | 2390628 B | 3/2004 |
| GB | 2347952 | A | 9/2000 | GB | 2391033 B | 3/2004 |
| GB | 2348223 | A | 9/2000 | GB | 2392686 A | 3/2004 |
| GB | 2348657 | A | 10/2000 | GB | 2393199 A | 3/2004 |
| GB | 2357099 | A | 12/2000 | GB | 2373524 B | 4/2004 |
| GB | 2356651 | A | 5/2001 | GB | 2390387 B | 4/2004 |
| GB | 2350137 | B | 8/2001 | GB | 2392686 B | 4/2004 |
| GB | 2361724 | | 10/2001 | GB | 2392691 B | 4/2004 |
| GB | 2365898 | A | 2/2002 | GB | 2391575 B | 5/2004 |
| GB | 2359837 | B | 4/2002 | GB | 2394979 A | 5/2004 |
| GB | 2370301 | A | 6/2002 | GB | 2395506 A | 5/2004 |
| GB | 2371064 | A | 7/2002 | GB | 2392932 B | 6/2004 |
| GB | 2371574 | A | 7/2002 | GB | 2395734 A | 6/2004 |
| GB | 2373524 | | 9/2002 | GB | 2396635 A | 6/2004 |
| GB | 2367842 | A | 10/2002 | GB | 2396639 A | 6/2004 |
| GB | 2374098 | A | 10/2002 | GB | 2396640 A | 6/2004 |
| GB | 2374622 | A | 10/2002 | GB | 2396641 A | 6/2004 |
| GB | 2375560 | A | 11/2002 | GB | 2396642 A | 6/2004 |
| GB | 2380213 | A | 4/2003 | GB | 2396643 A | 6/2004 |
| GB | 2380503 | A | 4/2003 | GB | 2396644 A | 6/2004 |
| GB | 2381019 | A | 4/2003 | GB | 2396646 A | 6/2004 |
| GB | 2343691 | B | 5/2003 | GB | 2373468 B | 7/2004 |
| GB | 2382828 | A | 6/2003 | GB | 2396869 A | 7/2004 |
| GB | 2344606 | B | 8/2003 | GB | 2397261 A | 7/2004 |
| GB | 2347950 | B | 8/2003 | GB | 2397262 A | 7/2004 |
| GB | 2380213 | B | 8/2003 | GB | 2397263 A | 7/2004 |

| | | | | | | |
|---|---|---|---|---|---|---|
| GB | 2397264 | A | 7/2004 | GB | 2410518 | A | 3/2005 |
| GB | 2397265 | A | 7/2004 | GB | 2389597 | B | 5/2005 |
| GB | 2390622 | B | 8/2004 | GB | 2399119 | B | 5/2005 |
| GB | 2398087 | A | 8/2004 | GB | 2399580 | B | 5/2005 |
| GB | 2398317 | A | 8/2004 | GB | 2401630 | B | 5/2005 |
| GB | 2398318 | A | 8/2004 | GB | 2401631 | B | 5/2005 |
| GB | 2398319 | A | 8/2004 | GB | 2401632 | B | 5/2005 |
| GB | 2398320 | A | 8/2004 | GB | 2401633 | B | 5/2005 |
| GB | 2398321 | A | 8/2004 | GB | 2401634 | B | 5/2005 |
| GB | 2398322 | A | 8/2004 | GB | 2401635 | B | 5/2005 |
| GB | 2398323 | A | 8/2004 | GB | 2401636 | B | 5/2005 |
| GB | 2398326 | A | 8/2004 | GB | 2401637 | B | 5/2005 |
| GB | 2382367 | B | 9/2004 | GB | 2401638 | B | 5/2005 |
| GB | 2396641 | B | 9/2004 | GB | 2401639 | B | 5/2005 |
| GB | 2396643 | B | 9/2004 | GB | 2408278 | A | 5/2005 |
| GB | 2397261 | B | 9/2004 | GB | 2399579 | B | 6/2005 |
| GB | 2397262 | B | 9/2004 | GB | 2409216 | A | 6/2005 |
| GB | 2397263 | B | 9/2004 | GB | 2409218 | A | 6/2005 |
| GB | 2397264 | B | 9/2004 | GB | 2401893 | B | 7/2005 |
| GB | 2397265 | B | 9/2004 | GB | 2414749 | A | 7/2005 |
| GB | 2399120 | A | 9/2004 | GB | 2414750 | A | 7/2005 |
| GB | 2399579 | A | 9/2004 | GB | 2414751 | A | 7/2005 |
| GB | 2399580 | A | 9/2004 | GB | 2 403970 | B | 8/2005 |
| GB | 2399848 | A | 9/2004 | GB | 2398326 | B | 8/2005 |
| GB | 2399849 | A | 9/2004 | GB | 2403971 | B | 8/2005 |
| GB | 2399850 | A | 9/2004 | GB | 2403972 | B | 8/2005 |
| GB | 2384502 | B | 10/2004 | GB | 2380503 | B | 10/2005 |
| GB | 2396644 | B | 10/2004 | GB | 2382828 | B | 10/2005 |
| GB | 2400126 | A | 10/2004 | GB | 2398317 | B | 10/2005 |
| GB | 2400393 | A | 10/2004 | GB | 2398318 | B | 10/2005 |
| GB | 2400624 | A | 10/2004 | GB | 2398319 | B | 10/2005 |
| GB | 2396640 | B | 11/2004 | GB | 2398321 | B | 10/2005 |
| GB | 2396642 | B | 11/2004 | GB | 2398322 | B | 10/2005 |
| GB | 2401136 | A | 11/2004 | GB | 2412681 | A | 10/2005 |
| GB | 2401137 | A | 11/2004 | GB | 2412682 | A | 10/2005 |
| GB | 2401138 | A | 11/2004 | GB | 2413136 | A | 10/2005 |
| GB | 2401630 | A | 11/2004 | GB | 2414493 | A | 11/2005 |
| GB | 2401631 | A | 11/2004 | GB | 2409217 | B | 12/2005 |
| GB | 2401632 | A | 11/2004 | GB | 2410518 | B | 12/2005 |
| GB | 2401633 | A | 11/2004 | GB | 2415003 | A | 12/2005 |
| GB | 2401634 | A | 11/2004 | GB | 2415219 | A | 12/2005 |
| GB | 2401635 | A | 11/2004 | GB | 2395506 | B | 1/2006 |
| GB | 2401636 | A | 11/2004 | GB | 2412681 | B | 1/2006 |
| GB | 2401637 | A | 11/2004 | GB | 2412682 | B | 1/2006 |
| GB | 2401638 | A | 11/2004 | GB | 2415979 | A | 1/2006 |
| GB | 2401639 | A | 11/2004 | GB | 2415983 | A | 1/2006 |
| GB | 2381019 | B | 12/2004 | GB | 2415987 | A | 1/2006 |
| GB | 2382368 | B | 12/2004 | GB | 2415988 | A | 1/2006 |
| GB | 2394979 | B | 12/2004 | GB | 2416177 | A | 1/2006 |
| GB | 2401136 | B | 12/2004 | GB | 2416361 | A | 1/2006 |
| GB | 2401137 | B | 12/2004 | GB | 2416556 | A | 2/2006 |
| GB | 2401138 | B | 12/2004 | GB | 2416794 | A | 2/2006 |
| GB | 2401971 | A | 1/2005 | GB | 2416795 | A | 2/2006 |
| GB | 2403970 | A | 1/2005 | GB | 2417273 | A | 2/2006 |
| GB | 2403972 | A | 1/2005 | GB | 2417275 | A | 2/2006 |
| GB | 2400624 | B | 2/2005 | GB | 2418216 | A | 3/2006 |
| GB | 2404402 | A | 2/2005 | GB | 2418217 | A | 3/2006 |
| GB | 2404676 | A | 2/2005 | GB | 2418690 | A | 4/2006 |
| GB | 2404680 | A | 2/2005 | GB | 2418941 | A | 4/2006 |
| GB | 2384807 | C | 3/2005 | GB | 2418942 | A | 4/2006 |
| GB | 2388134 | B | 3/2005 | GB | 2418943 | A | 4/2006 |
| GB | 2398320 | B | 3/2005 | GB | 2418944 | A | 4/2006 |
| GB | 2398323 | B | 3/2005 | GB | 2419907 | A | 5/2006 |
| GB | 2399120 | B | 3/2005 | GB | 2419913 | A | 5/2006 |
| GB | 2399848 | B | 3/2005 | GB | 2400126 | B | 6/2006 |
| GB | 2399849 | B | 3/2005 | GB | 2414749 | B | 6/2006 |
| GB | 2405893 | A | 3/2005 | GB | 2420810 | A | 6/2006 |
| GB | 2406117 | A | 3/2005 | GB | 2421257 | A | 6/2006 |
| GB | 2406118 | A | 3/2005 | GB | 2421258 | A | 6/2006 |
| GB | 2406119 | A | 3/2005 | GB | 2421259 | A | 6/2006 |
| GB | 2406120 | A | 3/2005 | GB | 2421262 | A | 6/2006 |
| GB | 2406125 | A | 3/2005 | GB | 2421529 | A | 6/2006 |
| GB | 2406126 | A | 3/2005 | GB | 2422164 | A | 7/2006 |

| | | | | | | | |
|---|---|---|---|---|---|---|---|
| GB | 2406599 | B | 8/2006 | SU | 1663179 | A2 | 7/1991 |
| GB | 2418690 | B | 8/2006 | SU | 1663180 | A1 | 7/1991 |
| GB | 2421257 | B | 8/2006 | SU | 1677225 | A1 | 9/1991 |
| GB | 2421258 | B | 8/2006 | SU | 1677248 | A1 | 9/1991 |
| GB | 2422859 | A | 8/2006 | SU | 1686124 | A1 | 10/1991 |
| GB | 2422860 | A | 8/2006 | SU | 1686125 | A1 | 10/1991 |
| GB | 2423317 | | 8/2006 | SU | 1688123 | A1 | 10/1991 |
| GB | 2414493 | B | 9/2006 | SU | 1698413 | A1 | 12/1991 |
| GB | 2424077 | A | 9/2006 | SU | 1710694 | A | 2/1992 |
| GB | 2408277 | A | 5/2008 | SU | 1730429 | A1 | 4/1992 |
| ID | P01.012.197/2005 | | 1/2005 | SU | 1745873 | A1 | 7/1992 |
| ID | 03.09.044.392/2005 | | 9/2005 | SU | 1747673 | A1 | 7/1992 |
| ID | 03.09.046.2804/2006 | | 8/2006 | SU | 1749267 | A1 | 7/1992 |
| JP | 208458 | | 10/1985 | SU | 1295799 | A1 | 2/1995 |
| JP | 6475715 | | 3/1989 | WO | WO81/00132 | | 1/1981 |
| JP | 102875 | | 4/1995 | WO | WO90/05598 | | 3/1990 |
| JP | 11-169975 | | 6/1999 | WO | WO92/01859 | | 2/1992 |
| JP | 94068 | A | 4/2000 | WO | WO92/08875 | | 5/1992 |
| JP | 107870 | A | 4/2000 | WO | WO93/25799 | | 12/1993 |
| JP | 162192 | | 6/2000 | WO | WO93/25800 | | 12/1993 |
| JP | 2001-47161 | | 2/2001 | WO | WO94/21887 | | 9/1994 |
| NL | 9001081 | | 12/1991 | WO | WO94/25655 | | 11/1994 |
| RO | 113267 | B1 | 5/1998 | WO | WO95/03476 | | 2/1995 |
| RU | 1786241 | A1 | 1/1993 | WO | WO96/01937 | | 1/1996 |
| RU | 1804543 | A3 | 3/1993 | WO | WO96/21083 | | 7/1996 |
| RU | 1810482 | A1 | 4/1993 | WO | WO96/26350 | | 8/1996 |
| RU | 1818459 | A1 | 5/1993 | WO | WO96/37681 | | 11/1996 |
| RU | 2016345 | C1 | 7/1994 | WO | WO97/06346 | | 2/1997 |
| RU | 2039214 | C1 | 7/1995 | WO | WO97/11306 | | 3/1997 |
| RU | 2056201 | C1 | 3/1996 | WO | WO97/17524 | | 5/1997 |
| RU | 2064357 | C1 | 7/1996 | WO | WO97/17526 | | 5/1997 |
| RU | 2068940 | C1 | 11/1996 | WO | WO97/17527 | | 5/1997 |
| RU | 2068943 | C1 | 11/1996 | WO | WO97/20130 | | 6/1997 |
| RU | 2079633 | C1 | 5/1997 | WO | WO97/21901 | | 6/1997 |
| RU | 2083798 | C1 | 7/1997 | WO | WO97/35084 | | 9/1997 |
| RU | 2091655 | C1 | 9/1997 | WO | WO98/00626 | | 1/1998 |
| RU | 2095179 | C1 | 11/1997 | WO | WO98/07957 | | 2/1998 |
| RU | 2105128 | C1 | 2/1998 | WO | WO98/09053 | | 3/1998 |
| RU | 2108445 | C1 | 4/1998 | WO | WO98/22690 | | 5/1998 |
| RU | 2144128 | C1 | 1/2000 | WO | WO98/26152 | | 6/1998 |
| SU | 350833 | | 9/1972 | WO | WO98/42947 | | 10/1998 |
| SU | 511468 | | 9/1976 | WO | WO98/49423 | | 11/1998 |
| SU | 607950 | | 5/1978 | WO | WO99/02818 | | 1/1999 |
| SU | 612004 | | 5/1978 | WO | WO99/04135 | | 1/1999 |
| SU | 620582 | | 7/1978 | WO | WO99/06670 | | 2/1999 |
| SU | 641070 | | 1/1979 | WO | WO99/08827 | | 2/1999 |
| SU | 909114 | | 5/1979 | WO | WO99/08828 | | 2/1999 |
| SU | 832049 | | 5/1981 | WO | WO99/18328 | | 4/1999 |
| SU | 853089 | | 8/1981 | WO | WO99/23354 | | 5/1999 |
| SU | 874952 | | 10/1981 | WO | WO99/25524 | | 5/1999 |
| SU | 894169 | | 1/1982 | WO | WO99/25951 | | 5/1999 |
| SU | 899850 | | 1/1982 | WO | WO99/35368 | | 7/1999 |
| SU | 907220 | | 2/1982 | WO | WO99/43923 | | 9/1999 |
| SU | 953172 | | 8/1982 | WO | WO00/01926 | | 1/2000 |
| SU | 959878 | | 9/1982 | WO | WO00/04271 | | 1/2000 |
| SU | 976019 | | 11/1982 | WO | WO00/08301 | | 2/2000 |
| SU | 976020 | | 11/1982 | WO | WO00/26500 | | 5/2000 |
| SU | 989038 | | 1/1983 | WO | WO00/26501 | | 5/2000 |
| SU | 1002514 | | 3/1983 | WO | WO00/26502 | | 5/2000 |
| SU | 1041671 | A | 9/1983 | WO | WO00/31375 | | 6/2000 |
| SU | 1051222 | A | 10/1983 | WO | WO00/37766 | | 6/2000 |
| SU | 1086118 | A | 4/1984 | WO | WO00/37767 | | 6/2000 |
| SU | 1077803 | A | 7/1984 | WO | WO00/37768 | | 6/2000 |
| SU | 1158400 | A | 5/1985 | WO | WO00/37771 | | 6/2000 |
| SU | 1212575 | A | 2/1986 | WO | WO00/37772 | | 6/2000 |
| SU | 1250637 | A1 | 8/1986 | WO | WO00/39432 | | 7/2000 |
| SU | 1324722 | A1 | 7/1987 | WO | WO00/46484 | | 8/2000 |
| SU | 1411434 | | 7/1988 | WO | WO00/50727 | | 8/2000 |
| SU | 1430498 | A1 | 10/1988 | WO | WO00/50732 | | 8/2000 |
| SU | 1432190 | A1 | 10/1988 | WO | WO00/50733 | | 8/2000 |
| SU | 1601330 | | 10/1990 | WO | WO00/77431 | A2 | 12/2000 |
| SU | 1627663 | A2 | 2/1991 | WO | WO01/04520 | A1 | 1/2001 |
| SU | 1659621 | A1 | 6/1991 | WO | WO01/04535 | A1 | 1/2001 |

| | | | | | | | |
|---|---|---|---|---|---|---|---|
| WO | WO01/18354 | A1 | 3/2001 | WO | WO2004/003337 | A1 | 1/2004 |
| WO | WO01/21929 | A1 | 3/2001 | WO | WO2004/009950 | A1 | 1/2004 |
| WO | WO01/26860 | A1 | 4/2001 | WO | WO2004/010039 | A2 | 1/2004 |
| WO | WO01/33037 | A1 | 5/2001 | WO | WO2004/010039 | A3 | 1/2004 |
| WO | WO01/38693 | A1 | 5/2001 | WO | WO2004/011776 | A2 | 2/2004 |
| WO | WO01/60545 | A1 | 8/2001 | WO | WO2004/011776 | A3 | 2/2004 |
| WO | WO01/83943 | A1 | 11/2001 | WO | WO2004/018823 | A2 | 3/2004 |
| WO | WO01/98623 | A1 | 12/2001 | WO | WO2004/018823 | A3 | 3/2004 |
| WO | WO02/01102 | A1 | 1/2002 | WO | WO2004/018824 | A2 | 3/2004 |
| WO | WO02/10550 | A1 | 2/2002 | WO | WO2004/018824 | A3 | 3/2004 |
| WO | WO02/10551 | A1 | 2/2002 | WO | WO2004/020895 | A2 | 3/2004 |
| WO | WO 02/20941 | A1 | 3/2002 | WO | WO2004/020895 | A3 | 3/2004 |
| WO | WO02/25059 | A1 | 3/2002 | WO | WO2004/023014 | A2 | 3/2004 |
| WO | WO02/29199 | A1 | 4/2002 | WO | WO2004/023014 | A3 | 3/2004 |
| WO | WO02/40825 | A1 | 5/2002 | WO | WO2004/026017 | A2 | 4/2004 |
| WO | WO02/053867 | A2 | 7/2002 | WO | WO2004/026017 | A3 | 4/2004 |
| WO | WO02/053867 | A3 | 7/2002 | WO | WO2004/026073 | A2 | 4/2004 |
| WO | WO02/059456 | A1 | 8/2002 | WO | WO2004/026073 | A3 | 4/2004 |
| WO | WO02/066783 | A1 | 8/2002 | WO | WO2004/026500 | A2 | 4/2004 |
| WO | WO02/068792 | A1 | 9/2002 | WO | WO2004/026500 | A3 | 4/2004 |
| WO | WO02/073000 | A1 | 9/2002 | WO | WO2004/027200 | A2 | 4/2004 |
| WO | WO02/075107 | A1 | 9/2002 | WO | WO2004/027200 | A3 | 4/2004 |
| WO | WO02/077411 | A1 | 10/2002 | WO | WO2004/027204 | A2 | 4/2004 |
| WO | WO02/081863 | A1 | 10/2002 | WO | WO2004/027204 | A3 | 4/2004 |
| WO | WO02/081864 | A2 | 10/2002 | WO | WO2004/027205 | A2 | 4/2004 |
| WO | WO02/086285 | A1 | 10/2002 | WO | WO2004/027205 | A3 | 4/2004 |
| WO | WO02/086286 | A2 | 10/2002 | WO | WO2004/027392 | A1 | 4/2004 |
| WO | WO02/090713 | | 11/2002 | WO | WO2004/027786 | A2 | 4/2004 |
| WO | WO02/095181 | A1 | 11/2002 | WO | WO2004/027786 | A3 | 4/2004 |
| WO | WO02/103150 | A2 | 12/2002 | WO | WO2004/053434 | A2 | 6/2004 |
| WO | WO03/004819 | A2 | 1/2003 | WO | WO2004/053434 | A3 | 6/2004 |
| WO | WO03/004819 | A3 | 1/2003 | WO | WO2004/057715 | A2 | 7/2004 |
| WO | WO03/004820 | A2 | 1/2003 | WO | WO2004/057715 | A3 | 7/2004 |
| WO | WO03/004820 | A3 | 1/2003 | WO | WO2004/067961 | A2 | 8/2004 |
| WO | WO03/008756 | A1 | 1/2003 | WO | WO2004/067961 | A3 | 8/2004 |
| WO | WO03/012255 | A1 | 2/2003 | WO | WO2004/072436 | A1 | 8/2004 |
| WO | WO03/016669 | A2 | 2/2003 | WO | WO2004/074622 | A2 | 9/2004 |
| WO | WO03/016669 | A3 | 2/2003 | WO | WO2004/074622 | A3 | 9/2004 |
| WO | WO03/023178 | A2 | 3/2003 | WO | WO2004/076798 | A2 | 9/2004 |
| WO | WO03/023178 | A3 | 3/2003 | WO | WO2004/076798 | A3 | 9/2004 |
| WO | WO03/023179 | A2 | 3/2003 | WO | WO2004/081346 | A2 | 9/2004 |
| WO | WO03/023179 | A3 | 3/2003 | WO | WO2004/083591 | A2 | 9/2004 |
| WO | WO03/029607 | A1 | 4/2003 | WO | WO2004/083591 | A3 | 9/2004 |
| WO | WO03/029608 | A1 | 4/2003 | WO | WO2004/083592 | A2 | 9/2004 |
| WO | WO03/036018 | A2 | 5/2003 | WO | WO2004/083592 | A3 | 9/2004 |
| WO | WO03/042486 | A2 | 5/2003 | WO | WO2004/083593 | A2 | 9/2004 |
| WO | WO03/042486 | A3 | 5/2003 | WO | WO2004/083594 | A2 | 9/2004 |
| WO | WO03/042487 | A2 | 5/2003 | WO | WO2004/083594 | A3 | 9/2004 |
| WO | WO03/042487 | A3 | 5/2003 | WO | WO2004/085790 | A2 | 10/2004 |
| WO | WO03/042489 | A2 | 5/2003 | WO | WO2004/089608 | A2 | 10/2004 |
| WO | WO03/048520 | A1 | 6/2003 | WO | WO2004/092527 | A2 | 10/2004 |
| WO | WO03/048521 | A2 | 6/2003 | WO | WO2004/092528 | A2 | 10/2004 |
| WO | WO03/055616 | A2 | 7/2003 | WO | WO2004/092528 | A3 | 10/2004 |
| WO | WO03/058022 | A2 | 7/2003 | WO | WO2004/092530 | A2 | 10/2004 |
| WO | WO03/058022 | A3 | 7/2003 | WO | WO2004/092530 | A3 | 10/2004 |
| WO | WO03/059549 | A1 | 7/2003 | WO | WO2004/094766 | A2 | 11/2004 |
| WO | WO03/064813 | A1 | 8/2003 | WO | WO2004/094766 | A3 | 11/2004 |
| WO | WO03/069115 | A3 | 8/2003 | WO | WO2005/017303 | A2 | 2/2005 |
| WO | WO03/071086 | A2 | 8/2003 | WO | WO2005/021921 | A2 | 3/2005 |
| WO | WO03/071086 | A3 | 8/2003 | WO | WO2005/021921 | A3 | 3/2005 |
| WO | WO03/078785 | A2 | 9/2003 | WO | WO2005/021922 | A2 | 3/2005 |
| WO | WO03/078785 | A3 | 9/2003 | WO | WO2005/021922 | A3 | 3/2005 |
| WO | WO03/086675 | A2 | 10/2003 | WO | WO2005/024141 | A3 | 3/2005 |
| WO | WO03/086675 | A3 | 10/2003 | WO | WO2005/024170 | A2 | 3/2005 |
| WO | WO03/089161 | A2 | 10/2003 | WO | WO2005/024170 | A3 | 3/2005 |
| WO | WO03/089161 | A3 | 10/2003 | WO | WO2005/024171 | A2 | 3/2005 |
| WO | WO03/093623 | A2 | 11/2003 | WO | WO2005/028803 | A2 | 3/2005 |
| WO | WO03/093623 | A3 | 11/2003 | WO | WO2005/071212 | A1 | 4/2005 |
| WO | WO03/102365 | A1 | 12/2003 | WO | WO2005/079186 | A2 | 9/2005 |
| WO | WO03/104601 | A2 | 12/2003 | WO | WO2005/079186 | A3 | 9/2005 |
| WO | WO03/104601 | A3 | 12/2003 | WO | WO2005/081803 | A2 | 9/2005 |
| WO | WO03/106130 | A2 | 12/2003 | WO | WO2005/086614 | A2 | 9/2005 |
| WO | WO03/106130 | A3 | 12/2003 | WO | WO2006/014333 | A2 | 2/2006 |

| | | | |
|---|---|---|---|
| WO | WO2006/020723 A2 | 2/2006 |
| WO | WO2006/020726 A2 | 2/2006 |
| WO | WO2006/020734 A2 | 2/2006 |
| WO | WO2006/020809 A2 | 2/2006 |
| WO | WO2006/020810 A2 | 2/2006 |
| WO | WO2006/020810 A3 | 2/2006 |
| WO | WO2006/020827 A2 | 2/2006 |
| WO | WO2006/020827 A3 | 2/2006 |
| WO | WO2006/020913 A2 | 2/2006 |
| WO | WO2006/020913 A3 | 2/2006 |
| WO | WO2006/020960 A2 | 2/2006 |
| WO | WO2006/033720 A2 | 3/2006 |
| WO | WO2004/089608 A3 | 7/2006 |
| WO | WO2006/079072 A2 | 7/2006 |
| WO | WO2006/088743 A2 | 8/2006 |
| WO | WO2006/102171 A2 | 9/2006 |
| WO | WO2006/102556 A2 | 9/2006 |

OTHER PUBLICATIONS

Yoon et al. "Low Cycle Fatique testing of 429EM stainless steel pipe" International Journal of Fatique, vol. 23, available online Oct. 23, 2003. Accessed May 11, 2008. pp. 1301-1307.*

Shah Khan et al. "Fracture Studies on High Hardness BISALLOY 500 Steel" 1983, Defence Scient and Technology Organization. <http://hdl.handle.net/1947/3302>.*

Valdes et al. "Selection of a Completion Material for a Sour Oil Field using Fracture Mechanics Concepts and Stress Corrosion Cracking Testing" Corrosion, 1998. <http://content.nace.org/Store/Downloads/98111.PDF>.*

Blasingame et al., "Solid Expandable Tubular Technology in Mature Basins," *Society of Petroleum Engineers* 2003.

Brass et al., "Water Production Management—PDO's Successful Application of Expandable Technology," *Society of Petroleum Engineers*, 2002.

Brock et al., "An Expanded Horizon," Hart's E&P, Feb. 2000.

Buckler et al., "Expandable Cased-hole Liner Remediates Prolific Gas Well and Minimizes Loss of Production," *Offshore Technology Conference*, 15151.

Bullock, "Advances Grow Expandable Applications," *The American Oil & Gas Reporter*, Sep. 2004.

Cales, "The Development and Applications of Solid Expandable Tubular Technology," *Enventure Global Technology*, Paper 2003-136, 2003.

Cales et al., "Reducing Non-Productive Time Through the Use of Solid Expandable Tubulars: How to Beat the Curve Through Pre-Planning," *Offshore Technology Conference*, 16669, 2004.

Cales et al., "Subsidence Remediation—Extending Well Life Through the Use of Solid Expandable Casing Systems," *AADE Houston Chapter*, Mar. 27, 2001.

Campo et al., "Case Histories—Drilling and Recompletion Applications Using Solid Expandable Tubular Technology," *Society of Petroleum Engineers*, SPE/IADC 72304; 2002.

Carstens et al., "Solid Expandable Tubular Technology: The Value of Planned Installations vs. Contingency,".

Case History, "Eemskanaal—2 Groningen," Enventure Global Technology, Feb. 2002.

Case History, "Graham Ranch No. 1 Newark East Barnett Field" Enventure Global Technology, Feb. 2002.

Case History, "K.K. Camel No. 1 Ridge Field Lafayette Parish, Louisiana," Enventure Global Technology, Feb. 2002.

Case History, "Mississippi Canyon 809 URSA TLP, OSC-G 5868, No. A-12," Enventure Global Technology, Mar. 2004.

Case History, "Unocal Sequoia Mississippi Canyon 941 Well No. 2" Enventure Global Technology, 2005.

Case History, "Yibal 381 Oman," Enventure Global Technology, Feb. 2002.

Cook, "Same Internal Casing Diameter From Surface to TD," *Offshore*, Jul. 2002.

Cottrill, "Expandable Tubulars Close in on the Holy Grail of Drilling," *Upstream*, Jul. 26, 2002.

Daigle et al., "Expandable Tubulars: Field Examples of Application in Well Construction and Remediation," *Society of Petroleum Engineers*, SPE 62958, 2000.

Daneshy, "Technology Strategy Breeds Value," E&P, May 2004.

Data Sheet, "Enventure Cased-Hole Liner (CHL) System" Enventure Global Technology, Dec. 2002.

Data Sheet, "Enventure Openhole Liner (OHL) System" Enventure Global Technology, Dec. 2002.

Data Sheet, "Window Exit Applications OHL Window Exit Expansion" Enventure Global Technology, Jun. 2003.

Dean et al., "Monodiameter Drilling Liner—From Concept to Reality," *Society of Petroleum Engineers*, SPE/IADC 79790, 2003.

Demong et al., "Breakthroughs Using Solid Expandable Tubulars to Construct Extended Reach Wells," *Society of Petroleum Engineers*, IADC/SPE 87209, 2004.

Demong et al., "Casing Design in Complex Wells: The Use of Expendables and Multilateral Technology to Attack the size Reduction Issue".

Demong et al., "Expandable Tubulars Enable Multilaterals Without Compromise on Hole Size," *Offshore*, Jun. 2003.

Demong et al., "Planning the Well Construction Process for the Use of Solid Expandable Casing," *Society of Petroleum Engineers*, SPE 85303, 2003.

Demoulin, "Les Tubes Expansibles Changent La Face Du Forage Petrolier," *L'Usine Nouvelle*, 2878:50-52, 3 Juillet 2003.

Dupal et al., "Realization of the MonoDiameter Well: Evolution of a Game-Changing Technology," *Offshore Technology Conference*, OTC 14312, 2002.

Dupal et al., "Solid Expandable Tubular Technology—A Year of Case Histories in the Drilling Environment," *Society of Petroleum Engineers*, SPE/IADC 67770, 2001.

Dupal et al., "Well Design with Expandable Tubulars Reduces Cost and Increases Success in Deepwater Applications," *Deep Offshore Technology*, 2000.

Duphorne, "Letter Re: Enventure Claims of Baker Infringement of Enventure's Expandable Patents," Apr. 1, 2005.

"EIS Expandable Isolation Sleeve" *Expandable Tubular Technology*, Feb. 2003.

Enventure Global Technology, Solid Expandable Tubulars are Enabling Technology, *Drilling Contractor*, Mar.-Apr. 2001.

"Enventure Ready to Rejuvinate the North Sea," *Roustabout*, Sep. 2004.

Escobar et al., "Increasing Solid Expandable Tubular Technology Reliability in a Myriad of Downhole Environments," *Society of Petroleum Engineers*, SPE/IADC 81094, 2003.

Etsion, "A Laser Surface Textured Hydrostatic Mechanical Seal," *Sealing Technology*, Mar. 2003.

"Expandable Casing Accesses Remote Reservoirs," *Petroleum Engineer International*, Apr. 1999.

"Expandable Sand Screens," *Weatherford Completion Systems*, 2002.

Filippov et al., "Expandable Tubular Solutions," *Society of Petroleum Engineers*, SPE 56500, 1999.

"First ever SET Workshop Held in Aberdeen," *Roustabout*, Oct. 2004.

Fischer, "Expandables and the Dream of the Monodiameter Well: A Status Report", *World Oil*, Jul. 2004.

Fontova, "Solid Expandable Tubulars (SET) Provide Value to Operators Worldwide in a Variety of Applications," *EP Journal of Technology*, Apr. 2005.

Fraunhofer Iwu, "Research Area: Sheet Metal Forming—Superposition of Vibrations," 2001.

Furlow, "Casing Expansion, Test Process Fine Tuned on Ultra-deepwater Well," *Offshore*, Dec. 2000.

Furlow, "Expandable Casing Program Helps Operator Hit TD With Larger Tubulars," *Offshore*, Jan. 2000.

Furlow, "Expandable Solid Casing Reduces Telescope Effect," *Offshore*, Aug. 1998.

Furlow, "Agbada Well Solid Tubulars Expanded Bottom Up, Screens Expanded Top Down," *Offshore*, 2002.

Grant et al., "Deepwater Expandable Openhole Liner Case Histories: Learnings Through Field Applications," *Offshore Technology Conference*, OCT 14218, 2002.

Gusevik et al., "Reaching Deep Reservoir Targets Using Solid Expandable Tubulars" *Society of Petroleum Engineers*, SPE 77612, 2002.
Halliburton Completion Products, 1996.
Haut et al., "Meeting Economic Challenges of Deepwater Drilling with Expandable-Tubular Technology," *Deep Offshore Technology Conference*, 1999.
Hull, "Monodiameter Technology Keeps Hole Diameter to TD," *Offshore* Oct. 2002.
"Innovators Chart the Course."
Langley, "Case Study: Value in Drilling Derived From Application-Specific Technology," Oct. 2004.
Linzell, "Trib-Gel A Chemical Cold Welding Agent," 1999.
Lohoefer et al., "Expandable Liner Hanger Provides Cost-Effective Alternative Solution," *Society of Petroleum Engineers*, IADC/SPE 59151, 2000.
Mack et al., "How in Situ Expansion Affects Casing and Tubing Properties," *World Oil*, Jul. 1999. pp. 69-71.
Mack et al., "In-Situ Expansion of Casing and Tubing—Effect on Mechanical Properties and Resistance to Sulfide Stress Cracking,".
Merritt, "Casing Remediation—Extending Well Life Through The Use of Solid Expandable Casing Systems."
Merritt et al., "Well Remediation Using Expandable Cased-Hole Liners", *World Oil.*, Jul. 2002.
Merritt et al., "Well Remediation Using Expandable Cased-Hole Liners- Summary of Case Histories".
Moore et al., "Expandable Liner Hangers: Case Histories," *Offshore Technology Conference*, OTC 14313, 2002.
Moore et al., "Field Trial Proves Upgrades to Solid Expandable Tubulars," *Offshore Technology Conference*, OTC 14217, 2002.
News Release, "Shell and Halliburton Agree to Form Company to Develop and Market Expandable Casing Technology," Jun. 3, 1998.
Nor, et at., "Transforming Conventional Wells to Bigbore Completions Using Solid Expandable Tubular Technology," *Offshore Technology Conference*, OTC 14315, 2002.
Patin et al., "Overcoming Well Control Challenges with Solid Expandable Tubular Technology," *Offshore Technology Conference*, OTC 15152, 2003.
Power Ultrasonics, "Design and Optimisation of An Ultrasonic Die System For Forming Metal Cans," 1999.
Ratliff, "Changing Safety Paradigms in the Oil and Gas Industry," *Society of Petroleum Engineers*, SPE 90828, 2004.
Rivenbark, "Expandable Tubular Technology—Drill Deeper, Farther, More Economically," Enventure Global Technology.
Rivenbark et al., "Solid Expandable Tubular Technology: The Value of Planned Installation vs. Contingency," *Society of Petroleum Engineers*, SPE 90821, 2004.
Rivenbark et al., "Window Exit Sidetrack Enhancements Through the Use of Solid Expandable Casing," *Society of Petroleum Engineers*, IADC/SPE 88030, 2004.
Roca et al., "Addressing Common Drilling Challenges Using Solid Expandable Tubular Technology," *Society of Petroleum Engineers*, SPE 80446, 2003.
Sanders et al., Practices for Providing Zonal Isolation in Conjunction with Expandable Casing Jobs-Case Histories, 2003.
Sanders et al., "Three Diverse Applications on Three Continents for a Single Major Operator," *Offshore Technology Conference*, OTC 16667, 2004.
"SET Technology: The Facts" 2004.
Siemers et al., "Development and Field Testing of Solid Expandable Corrosion Resistant Cased-hole Liners to Boost Gas Production in Corrosive Environments," *Offshore Technology Conference*, OTC 15149, 2003.
"Slim Well:Stepping Stone to MonoDiameter," *Hart's E&P*, Jun. 2003.
Smith, "Pipe Dream Reality," *New Technology Magazine*, Dec. 2003.
"Solid Expandable Tubulars," *Hart's E&P*, Mar. 2002.
Sparling et al., "Expanding Oil Field Tubulars Through a Window Demonstrates Value and Provides New Well Construction Option," *Offshore Technology Conference*, OTC 16664, 2004.
Sumrow, "Shell Drills World's First Monodiameter Well in South Texas," *Oil and Gas*, Oct. 21, 2002.
Touboul et al., "New Technologies Combine to Reduce Drilling Cost in Ultradeepwater Applications," *Society of Petroleum Engineers*, SPE 90830, 2004.
Turcotte et al., "Geodynamics Applications of Continuum Physics to Geological Problems," 1982.
Van Noort et al., "Using Solid Expandable Tubulars for Openhole Water Shutoff," *Society of Petroleum Engineers*, SPE 78495, 2002.
Van Noort et al., "Water Production Reduced Using Solid Expandable Tubular Technology to "Clad," in Fractured Carbonate Formation" *Offshore Technology Conference*, OTC 15153, 2003.
Von Flatern, "From Exotic to Routine—the Offshore Quick-step," *Offshore Engineer*, Apr. 2004.
Von Flatern, "Oilfield Service Trio Target Jules Verne Territory," *Offshore Engineer*, Aug. 2001.
Waddell et al., "Advances in Single-diameter Well Technology: The Next Step to Cost-Effective Optimization," *Society of Petroleum Engineers*, SPE 90818, 2004.
Waddell et al., "Installation of Solid Expandable Tubular Systems Through Milled Casing Windows," *Society of Petroleum Engineers*, IADC/SPE 87208, 2004.
Williams, "Straightening the Drilling Curve," *Oil and Gas Investor*, Jan. 2003.
www.JETLUBE.com, "Oilfield Catalog—Jet-Lok Product Applicatin Descriptions," 1998.
www.MITCHMET.com, "3d Surface Texture Parameters," 2004.
"Expand Your Opportunities." *Enventure*. CD-ROM. Jun. 1999.
"Expand Your Opportunities." *Enventure*. CD-ROM. May 2001.
International Search Report, Application PCT/US04/00631, Mar. 28, 2005.
International Preliminary Examination Report, Application PCT/US02/24399, Aug. 6, 2004.
International Preliminary Examination Report, Application PCT/US02/25608, Jun. 1, 2005.
International Preliminary Examination Report, Application PCT/US02/25727, Jul. 7, 2004.
International Preliminary Examination Report PCT/US02/36157, Apr. 14, 2004.
International Preliminary Examination Report, Application PCT/US02/36267, Jan. 4, 2004.
International Preliminary Examination Report, Application PCT/US02/39418, Feb. 18, 2005.
International Preliminary Examination Report, Application PCT/US03/04837, Dec. 9, 2004.
International Preliminary Examination Report, Application PCT/US03/06544, May 10, 2005.
International Preliminary Examination Report, Application PCT/US03/10144, Jul. 7, 2004.
International Preliminary Examination Report, Application PCT/US03/11765, Dec. 10, 2004.
International Preliminary Examination Report, Application PCT/US03/11765, Jan. 25, 2005.
International Preliminary Examination Report, Application PCT/US03/11765, Jul. 18, 2005.
International Preliminary Examination Report, Application PCT/US01/11765, Aug. 15, 2005 (Corrected).
International Preliminary Examination Report, Application PCT/US03/13787, Mar. 2, 2005.
International Preliminary Examination Report, Application PCT/US03/13787, Apr. 7, 2005.
International Preliminary Examination Report, Application PCT/US03/14153, May 12, 2005.
International Preliminary Examination Report, Application PCT/US03/15020, May 9, 2005.
International Preliminary Examination Report, Application PCT/US03/20870, Sep. 30, 2004.
International Preliminary Examination Report, Application PCT/US03/25667, May 25, 2005.
International Preliminary Examination Report, Application PCT/US03/25675, Aug. 30, 2005.
International Preliminary Examination Report, Application PCT/US03/25676, Aug. 17, 2004.
International Preliminary Examination Report, Application PCT/US03/25677, Aug. 17, 2004.

International Preliminary Examination Report, Application PCT/US03/25742, Dec. 20, 2004.
International Preliminary Examination Report, Application PCT/US03/29460, Dec. 8, 2004.
International Preliminary Examination Report, Application PCT/US03/29858, May 23, 2005.
International Preliminary Examination Report, Application PCT/US03/29859, Aug. 16, 2004.
International Preliminary Examination Report, Application PCT/US03/38550, May 23, 2005.
International Preliminary Report on Patentability, Application PCT/US04/02122, May 13, 2005.
International Preliminary Report on Patentability, Application PCT/US04/08030, Jun. 10, 2005.
International Preliminary Report on Patentability, Application PCT/US04/08073, May 9, 2005.
International Preliminary Report on Patentability, Application PCT/US04/008170, Sep. 29, 2005.
International Preliminary Report on Patentability, Application PCT/US04/08171, Sep. 13, 2005.
International Preliminary Report on Patentability, Application PCT/US04/11177, Jun. 9, 2005.
International Preliminary Report on Patentability, Application PCT/US04/28438, Sep. 20, 2005.
Written Opinion to Application No. PCT/US03/25675, May 9, 2005.
Combined Search Report and Written Opinion to Application No. PCT/US04/10762, Sep. 1, 2005.
Combined Search Report and Written Opinion to Application No. PCT/US04/11973, Sep. 27, 2005.
Combined Search Report and Written Opinion to Application No. PCT/US04/28423, Jul. 13, 2005.
Search Report to Application No. GB 0415835.8, Dec. 2, 2004.
Search Report to Application No. GB 0415835.8, Mar. 10, 2005.
Examination Report to Application No. GB 0400018.8, May 17, 2005.
Examination Report to Application No. GB 0400019.6, May 19, 2005.
Examination Report to Application No. GB 0403891.5, Jun. 30, 2005.
Examination Report to Application No. GB 0404796.5, Apr. 14, 2005.
Examination Report to Application No. GB 0406257.6, Jun. 16, 2005.
Examination Report to Application No. GB 0406257.6, Sep. 2, 2005.
Examination Report to Application No. GB 0406258.4, Jul. 27, 2005.
Examination Report to Application No. GB 0408672.4, Mar. 21, 2005.
Examination Report to Application No. GB 0412533.2, May 20, 2005.
Examination Report to Application No. GB 0428141.6, Sep. 15, 2005.
Examination Report to Application No. GB 0500184.7, Sep. 12, 2005.
Examination Report to Application No. GB 0500600.2, Sep. 6, 2005.
Examination Report to Application No. GB 0501667.0, May 27, 2005.
Examination Report to Application No. GB 0503470.7, Sep. 22, 2005.
Examination Report to Application No. GB 0506699.8, Sep. 21, 2005.
Examination Report to Application No. GB 0507979.3, Jun. 16, 2005.
Search and Examination Report to Application No. GB 0425948.7, Apr. 14, 2005.
Search and Examination Report to Application No. GB 0425951.1, Apr. 14, 2005.
Search and Examination Report to Application No. GB 0425956.0, Apr. 14, 2005.
Search and Examination Report to Application No. GB 0505039.8, Jul. 22, 2005.
Search and Examination Report to Application No. GB 0506697.2, May 20, 2005.
Search and Examination Report to Application No. GB 0506700.4, Sep. 20, 2005.
Search and Examination Report to Application No. GB 0509618.5, Sep. 27, 2005.
Search and Examination Report to Application No. GB 0509620.1, Sep. 27, 2005.
Search and Examination Report to Application No. GB 0509626.8, Sep. 27, 2005.
Search and Examination Report to Application No. GB 0509627.6, Sep. 27, 2005.
Search and Examination Report to Application No. GB 0509629.2, Sep. 27, 2005.
Search and Examination Report to Application No. GB 0509630.0, Sep. 27, 2005.
Search and Examination Report to Application No. GB 0509631.8, Sep. 27, 2005.
Search and Examination Report to Application No. GB 0512396.3, Jul. 26, 2005.
Search and Examination Report to Application No. GB 0512398.9, Jul. 27, 2005.
Examination Report to Application No. AU 2001278196 ,Apr. 21, 2005.
Examination Report to Application No. AU 2002237757 ,Apr. 28, 2005.
Examination Report to Application No. AU 2002240366 ,Apr. 13, 2005.
Search Report to Application No. EP 02806451.7; Feb. 9, 2005.
Search Report to Application No. Norway 1999 5593, Aug. 20, 2002.
Adams, "Drilling Engineering: A Complete Well Planning Approach," 1985.
Enventure Global Technology, "SET Technology: The Facts," 2004.
Flatern, "Oilfield Service Trio Target Jules Verne Territory," at http://www.oilonline.com.
Harris, "Tube Welding." At http://www.tubenet.org.uk.technical.ewi.html.
Mohawk Energy, :Minimizing Drilling Ecoprints Houston, Dec. 16, 2005.
www.RIGZONE.com/news/article.asp?a_id=1755, "Tesco Provides Casing Drilling Operations Update," 2001.
www.RIGZONE.com/news/article.asp?a_id=2603, Conoco and Tesco Unveil Revolutionary Drilling Rig 2002.
International Search Report, Application PCT/US03/15020, Nov. 14, 2005.
International Preliminary Examination Report, Application PCT/US01/28690, Sep. 4, 2003.
International Preliminary Examination Report, Application PCT/US02/39425, Nov. 16, 2005.
International Preliminary Examination Report, Application PCT/US03/15020 (corrected), Nov. 14, 2004.
International Preliminary Report on Patentability, Application PCT/US04/00631, Mar. 2, 2006.
International Preliminary Report on Patentability, Application PCT/US04/04740, Jun. 27, 2006.
International Preliminary Report on Patentability, Application PCT/US04/10317, Jun. 23, 2006.
International Preliminary Report on Patentability, Application PCT/US04/028423, Mar. 9, 2006.
International Preliminary Report on Patentability, Application PCT/US04/028423, Jun. 19, 2006.
International Preliminary Report on Patentability, Application PCT/US04/28889, Aug. 1, 2006.
Combined Search Report and Written Opinion to Application No. PCT/US04/00631, Mar. 28, 2005.
Combined Search Report and Written Opinion to Application No. PCT/US04/10317, May 25, 2006.
Combined Search Report and Written Opinion to Application No. PCT/US04/28831, Dec. 19, 2005.
Combined Search Report and Written Opinion to Application No. PCT/US04/28889, Nov. 14, 2005.
Combined Search Report and Written Opinion to Application No. PCT/US05/28473, Sep. 1, 2006.
Combined Search Report and Written Opinion to Application No. PCT/US05/28642, Jul. 14, 2006.

Combined Search Report and Written Opinion to Application No. PCT/US05/28819, Aug. 3, 2006.
Combined Search Report and Written Opinion to Application No. PCT/US05/28869, Apr. 17, 2006.
Combined Search Report and Written Opinion to Application No. PCT/US06/04809, Aug. 29, 2006.
Search Report to Application No. GB 0507980.1, Apr. 24, 2006.
Examination Report to Application No. GB 0219757.2, Oct. 31, 2004.
Examination Report to Application No. GB 03723674.2, Feb. 6, 2006.
Examination Report to Application No. GB 0400019.6, Nov. 4, 2005.
Examination Report to Application No. GB 0406257.6, Sep. 2, 2005.
Examination Report to Application No. GB 0406257.6, Nov. 9, 2005.
Examination Report to Application No. GB 0406257.6, Apr. 28, 2006.
Examination Report to Application No. GB 0406258.4, Dec. 20, 2005.
Examination Report to Application No. GB 0412876.5, Feb. 13, 2006.
Examination Report to Application No. GB 0415835.8, Dec. 23, 2005.
Examination Report to Application No. GB 0422419.2, Nov. 8, 2005.
Examination Report to Application No. GB 0422893.8, Aug. 8, 2005.
Examination Report to Application No. GB 0422893.8, Dec. 15, 2005.
Examination Report to Application No. GB 0425948.7, Nov. 24, 2005.
Examination Report to Application No. GB 0425956.0, Nov. 24, 2005.
Examination Report to Application No. GB 0428141.6, Feb. 9, 2005.
Examination Report to Application No. GB 0428141.6, Feb. 21, 2006.
Examination Report to Application No. GB 05428141.6, Jul. 18, 2006.
Examination Report to Application No. GB 0500275.3, Apr. 5, 2006.
Examination Report to Application No. GB 0501667.0, Jan. 27, 2006.
Examination Report to Application No. GB 0503250.3, Nov. 15, 2005.
Examination Report to Application No. GB 0503250.3, Mar. 2, 2006.
Examination Report to Application No. GB 0503250.3, Aug. 11, 2006.
Examination Report to Application No. GB 0506699.8, May 11, 2006.
Examination Report to Application No. GB 0506700.4, May 16, 2006.
Examination Report to Application No. GB 0506702.0, May 11, 2006.
Examination Report to Application No. GB 0507979.3, Jun. 16, 2005.
Examination Report to Application No. GB 0507979.3, Jan. 17, 2006.
Examination Report to Application No. GB 0507979.3, Jun. 6, 2006.
Examination Report to Application No. GB 0507980.1, Sep. 29, 2005.
Examination Report to Application No. GB 0509618.5, Feb. 3, 2006.
Examination Report to Application No. GB 0509620.1, Feb. 14, 2006.
Examination Report to Application No. GB 0509627.6, Feb. 3, 2006.
Examination Report to Application No. GB 0509629.2, Feb. 3, 2006.
Examination Report to Application No. GB 0509630.0, Feb. 3, 2006.
Examination Report to Application No. GB 0509630.0, May 11, 2006.
Examination Report to Application No. GB 0509630.0, Jun. 6, 2006.
Examination Report to Application No. GB 0509631.8, Feb. 14, 2006.
Examination Report to Application No. GB 0517448.7, Nov. 9, 2005.
Examination Report to Application No. GB 0517448.7, Jul. 19, 2006.
Examination Report to Application No. GB 0518025.2, Oct. 27, 2005.
Examination Report to Application No. GB 0518025.2, May 25, 2006.
Examination Report to Application No. GB 0518039.3, Nov. 29, 2005.
Examination Report to Application No. GB 0518039.3, Aug. 2, 2006.
Examination Report to Application No. GB 0518252.2, Oct. 28, 2005.
Examination Report to Application No. GB 0518252.2, May 25, 2006.
Examination Report to Application No. GB 0518799.2, Nov. 9, 2005.
Examination Report to Application No. GB 0518799.2, Jun. 14, 2006.
Examination Report to Application No. GB 0518893.3, Dec. 16, 2005.
Examination Report to Application No. GB 0518893.3, Jul. 28, 2006.
Examination Report to Application No. GB 0519989.8, Mar. 8, 2006.
Examination Report to Application No. GB 0521024.0, Dec. 22, 2005.
Examination Report to Application No. GB 0522050.4. Dec. 13, 2005.
Examination Report to Application No. GB 0522892.9, Aug. 14, 2006.
Examination Report to Application No. GB 0602877.3, Mar. 20, 2006.
Examination Report to Application No. GB 0603576.0, Apr. 5, 2006.
Examination Report to Application No. GB 0603656.0, May 3, 2006.
Examination Report to Application No. GB 0603995.2, Apr. 25, 2006.
Examination Report to Application No. GB 0603996.0, Apr. 27, 2006.
Examination Report to Application No. GB 0604357.4, Apr. 27, 2006.
Examination Report to Application No. GB 0604359.0, Apr. 27, 2006.
Examination Report to Application No. GB 0604360.8, Apr. 26, 2006.
Search and Examination Report to Application No. GB 0412876.5, Sep. 27, 2005.
Search and Examination Report to Application No. GB 0507980.1, Jun. 20, 2006.
Search and Examination Report to Application No. GB 0516429.8, Nov. 7, 2005.
Search and Examination Report to Application No. GB 0516430.6, Nov. 8, 2005.
Search and Examination Report to Application No. GB 0516431.4, Nov. 8, 2005.
Search and Examination Report to Application No. GB 0522052.0, Aug. 8, 2006.
Search and Examination Report to Application No. GB 0522155.1, Mar. 7, 2006.
Search and Examination Report to Application No. GB 0522892.9 Jan. 5, 2006.
Search and Examination Report to Application No. GB 0523075.0, Jan. 12, 2006.
Search and Examination Report to Application No. GB 0523076.8, Dec. 14, 2005.
Search and Examination Report to Application No. GB 0523078.4, Dec. 13, 2005.
Search and Examination Report to Application No. GB 0523132.9, Jan. 12, 2006.
Search and Examination Report to Application No. GB 0524692.1, Dec. 19, 2005.
Search and Examination Report to Application No. GB 0525768.8, Feb. 3, 2006.
Search and Examination Report to Application No. GB 0525770.4, Feb. 3, 2006.
Search and Examination Report to Application No. GB 0525772.0, Feb. 2, 2006.
Search and Examination Report to Application No. GB 0525774.6, Feb. 2, 2006.
Search and Examination Report to Application No. GB 0602877.3, Sep. 25, 2006.
Search and Examination Report to Application No. GB 0609173.0, Jul. 19, 2006.

Examination Report to Application No. AU 2003257878, Jan. 19, 2006.
Examination Report to Application No. AU 2003257878, Jan. 30, 2006.
Examination Report to Application No. AU 2003257881, Jan. 19, 2006.
Examination Report to Application No. AU 2003257881, Jan. 30, 2006.
Examination Report to Application No. AU 2004202805, Jun. 14, 2006.
Examination Report to Application No. AU 2004202809, Jun. 14, 2006.
Examination Report to Application No. AU 2004202812, Jun. 14, 2006.
Examinaton Report to Application No. AU 2004202813, Jun. 14, 2006.
Examination Report to Application No. AU 2004202815, Jun. 14, 2006.
Search Report to Application No. EP 03071281.2; Nov. 7, 2005.
Search Report to Application No. EP 03071281.2; Nov. 14, 2005.
Search Report to Application No. EP 03723674.2; Nov. 22, 2005.
Search Report to Application No. EP 03723674.2; May 2, 2006.
Search Report to Application No. EP 03728326.4; Mar. 13, 2006.
Search Report to Application No. EP 03728326.4; Apr. 24, 2006.
Search Report to Application No. EP 03752486.5; Feb. 8, 2006.
Examination Report to Application No. EP 03752486.5; Jun. 28, 2006.
Search Report to Application No. EP 03759400.9; Mar. 3, 2006.
Search Report to Application No. EP 03759400.9; Mar. 24, 2006.
Search Report to Application No. EP 03793078.1; Mar. 21, 2006.
Search Report to Application No. EP 03793078.1; Jun. 16, 2006.
Examination Report to Application No. Norway 2002 1613, May 13, 2006.
Halliburton Energy Services, "Halliburton Completion Products" 1996, Page Packers 5-37, United States of America.
Turcotte and Schubert, Geodynamics (1982) John Wiley & Sons, Inc., pp. 9, 432.
Baker Hughes Incorporated, "EXPatch Expandable Cladding System" (2002).
Baker Hughes Incorporated, "EXPress Expandable Screen System".
High-Tech Wells, "World's First Completion Set Inside Expandable Screen" (2003) Gilmer, J.M., Emerson, A.B.
Baker Hughes Incorporated, "Technical Overview Production Enhancement Technology" (Mar. 10, 2003) Geir Owe Egge.
Baker Hughes Incorporated, "FORMlock Expandable Liner Hangers".
Weatherford Completion Systems, "Expandable Sand Screens" (2002).
Expandable Tubular Technology, "EIS Expandable Isolation Sleeve" (Feb. 2003).
Oilfield Catalog; "Jet-Lok Product Application Description" (Aug. 8, 2003).
Power Ultrasonics, "Design and Optimisation of an Ultrasonic Die System for Form" Chris Cheers (1999, 2000).
Research Area—Sheet Metal Forming—Superposition of Vibra; Fraunhofer IWU (2001).
Research Projects; "Analysis of Metal Sheet Formability and It's Factors of Influence" Prof. Dorel Banabic (2003).
www.materialsresources.com, "Low Temperature Bonding of Dissimilar and Hard-to-Bond Materials and Metal-Including.." (2004).
www.tribtech.com. "Trib-gel A Chemical Cold Welding Agent" G R Linzell (Sep. 14, 1999).
www.spurind.com, "Galvanic Protection, Metallurgical Bonds, Custom Fabrication—Spur Industries" (2000).
Lubrication Engineering, "Effect of Micro-Surface Texturing on Breakaway Torque and Blister Formation on Carbon-Graphite Faces in a Mechanical Seal" Philip Guichelaar, Karalyn Folkert, Izhak Etsion, Steven Pride (Aug. 2002).
Surface Technologies Inc., "Improving Tribological Performance of Mechanical Seals by Laser Surface Texturing" Izhak Etsion.
Tribology Transactions "Experimental Investigation of Laser Surface Texturing for Reciprocating Automotive Components" G Ryk, Y Klingerman and I Etsion (2002).
Proceeding of the International Tribology Conference, "Microtexturing of Functional Surfaces for Improving Their Tribological Performance" Henry Haefke, Yvonne Gerbig, Gabriel Dumitru and Valerio Romano (2002).
Sealing Technology, "A laser surface textured hydrostatic mechanical seal" Izhak Etsion and Gregory Halperin (Mar. 2003).
Metalforming Online, "Advanced Laser Texturing Tames Tough Tasks" Harvey Arbuckle.
Tribology Transactions, "A Laser Surface Textured Parallel Thrust Bearing" V. Brizmer, Y. Klingerman and I. Etsion (Mar. 2003).
PT Design, "Scratching the Surface" Todd E. Lizotte (Jun. 1999).
Tribology Transactions, "Friction-Reducing Surface-Texturing in Reciprocating Automotive Components" Aviram Ronen, and Izhak Etsion (2001).
Michigan Metrology "3D Surface Finish Roughness Texture Wear WYKO Veeco" C.A. Brown, PhD; Charles, W.A. Johnsen, S. Chester.
Letter From Baker Oil Tools to William Norvell in Regards to Enventure's Claims of Baker Infringement Of Enventure's Expandable Patents Apr. 1, 2005.
International Search Report, Application PCT/IL00/00245, Sep. 18, 2000.
International Search Report, Application PCT/US00/18635, Nov. 24, 2000.
International Search Report, Application PCT/US00/27645, Dec. 29, 2000.
International Search Report, Application PCT/US00/30022, Mar. 27, 2001.
International Search Report, Application PCT/US01/04753, Jul. 3, 2001.
International Search Report, Application PCT/US01/19014, Nov. 23, 2001.
International Search Report, Application PCT/US01/23815, Nov. 16, 2001.
International Search Report, Application PCT/US01/28960, Jan. 22, 2002.
International Search Report, Application PCT/US01/30256, Jan. 3, 2002.
International Search Report, Application PCT/US01/41446, Oct. 30, 2001.
International Search Report, Application PCT/US02/00093, Aug. 6, 2002.
International Search Report, Application PCT/US02/00677, Jul. 17, 2002.
International Search Report, Application PCT/US02/00677, Feb. 24, 2004.
International Search Report, Application PCT/US02/04353, Jun. 24, 2002.
International Search Report, Application PCT/US02/20256, Jan. 3, 2003.
International Search Report, Application PCT/US02/20477; Oct. 31, 2003.
International Search Report, Application PCT/US02/20477; Apr. 6, 2004.
International Search Report, Application PCT/US02/24399; Feb. 27, 2004.
International Examination Report, Application PCT/US02/24399, Aug. 6, 2004.
International Search Report, Application PCT/US02/25608; May 24, 2004.
International Search Report, Application PCT/US02/25727; Feb. 19, 2004.
Examination Report, Application PCT/US02/25727; Jul. 7, 2004.
International Search Report, Application PCT/US02/29856, Dec. 16, 2002.
International Search Report, Application PCT/US02/36157; Sep. 29, 2003.
International Search Report, Application PCT/US02/36157; Apr. 14, 2004.
International Search Report, Application PCT/US02/36267; May 21, 2004.
International Examination Report, Application PCT/US02/36267, Jan. 4, 2004.

International Search Report, Application PCT/US02/39418, Mar. 24, 2003.
International Examination Report, Application PCT/US02/39418, Feb. 18, 2005.
International Search Report, Application PCT/US02/39425, May 28, 2004.
International Search Report, Application PCT/US03/00609, May 20, 2004.
International Search Report, Application PCT/US03/04837, May 28, 2004.
International Examination Report, Application PCT/US03/04837, Dec. 9, 2004.
International Search Report, Application PCT/US03/06544, Jun. 9, 2004.
International Search Report, Application PCT/US03/10144; Oct. 31, 2003.
Examination Report, Application PCT/US03/10144; Jul. 7, 2004.
International Search Report, Application PCT/US03/11765; Nov. 13, 2003.
International Examination Report, Application PCT/US03/11765; Dec. 10, 2004.
International Examination Report, Application PCT/US03/11765;; Jan. 25, 2005.
International Search Report, Application PCT/US03/13787; May 28, 2004.
International Examination Report, Application PCT/US03/13787; Apr. 7, 2005.
International Examination Report, Application PCT/US03/13787; Mar. 2, 2005.
International Search Report, Application PCT/US03/14153; May 28, 2004.
International Search Report, Application PCT/US03/15020; Jul. 30, 2003.
International Search Report, Application PCT/US03/18530; Jun. 24, 2004.
International Search Report, Application PCT/US03/19993; May 24, 2004.
International Search Report, Application PCT/US03/20694; Nov. 12, 2003.
International Search Report, Application PCT/US03/20870; May 24, 2004.
International Search Report, Application PCT/US03/20870; Sep. 30, 2004.
International Search Report, Application PCT/US03/24779; Mar. 3, 2004.
International Search Report, Application PCT/US03/25675; May 25, 2004.
International Search Report, Application PCT/US03/25676; May 17, 2004.
International Examination Report, Application PCT/US03/25676, Aug. 17, 2004.
International. Search Report, Application PCT/US03/25677; May 21, 2004.
International Examination Report, Application PCT/US03/25677, Aug. 17, 2004.
International Search Report, Application PCT/US03/25707; Jun. 23, 2004.
International Search Report, Application PCT/US03/25715; Apr. 9, 2004.
International Search Report, Application PCT/US03/25716; Jan. 13, 2005.
International Search Report, Application PCT/US03/25742; May 27, 2004.
International Search Report, Application PCT/US03/25742; Dec. 20, 2004.
International Search Report, Application PCT/US03/29460; May 25, 2004.
International Examination Report, Application PCT/US03/29460; Dec. 8, 2004.
International Search Report, Application PCT/US03/25667; Feb. 26, 2004.
International Search Report, Application PCT/US03/29858; Jun. 30, 2003.
International Search Report, Application PCT/US03/29859; May 21, 2004.
International Examination Report, Application PCT/US03/29859, Aug. 16, 2004.
International Search Report, Application PCT/US03/38550; Jun. 15, 2004.
International Preliminary Report on Patentability, Application PCT/US04/04740; Apr. 27, 2005.
International Preliminary Report on Patentability, Application PCT/US04/06246; May 5, 2005.
International Preliminary Report on Patentability, Application PCT/US04/08030; Apr. 7, 2005.
Search Report to Application No. EP 02806451.7; Feb. 9, 2005.
Search Report to Application No. GB 0003251.6, Jul. 13, 2000.
Search Report to Application No. GB 0004282.0, Jul. 31, 2000.
Search Report to Application No. GB 0004282.0 Jan. 15, 2001.
Search and Examination Report to Application No. GB 0004282.0, Jun. 3, 2003.
Search Report to Application No. GB 0004285.3, Jul. 12, 2000.
Search Report to Application No. GB 0004285.3, Jan. 17, 2001.
Search Report to Application No. GB 0004285.3, Jan. 19, 2001.
Search Report to Application No. GB 0004285.3, Aug. 28, 2002.
Examination Report to Application No. 0004285.3, Mar. 28, 2003.
Examination Report to Application No. GB 0005399.1; Jul. 24, 2000.
Search Report to Application No. GB 0005399.1, Feb. 15, 2001.
Examination Report to Application No. GB 0005399.1; Oct. 14, 2002.
Search Report to Application No. GB 0013661.4, Oct. 20, 2000.
Search Report to Application No. GB 0013661.4, Apr. 17, 2001.
Search Report to Application No. GB 0013661.4, Feb. 19, 2003.
Examination Report to Application No. GB 0013661.4, Nov. 25, 2003.
Search Report to Application No. GB 0013661.4, Oct. 20, 2003.
Examination Report to Application No. GB 0208367.3, Apr. 4, 2003.
Examination Report to Application No. GB 0208367.3, Nov. 4, 2003.
Examination Report to Application No. GB 0208367.3, Nov. 17, 2003.
Examination Report to Application No. GB 0208367.3, Jan. 30, 2004.
Examination Report to Application No. GB 0212443.6, Apr. 10, 2003.
Examination Report to Application No. GB 0216409.3, Feb. 9, 2004.
Search Report to Application No. GB 0219757.2, Nov. 25, 2002.
Search Report to Application No. GB 0219757.2, Jan. 20, 2003.
Examination Report to Application No. GB 0219757.2, May 10, 2004.
Search Report to Application No. GB 0220872.6, Dec. 5, 2002.
Search Report to Application GB 0220872.8, Mar. 13, 2003.
Examination Report to Application GB 0220872.6, Oct. 29, 2004.
Search Report to Application No. GB 0225505.7, Mar. 5, 2003.
Search and Examination Report to Application No. GB 0225505.7, Jul. 1, 2003.
Examination Report to Application No. GB 0225505.7, Oct. 27, 2004.
Examination Report to Application No. GB 0225505.7 Feb. 15, 2005.
Examination Report to Application No. GB 0300085.8, Nov. 28, 2003.
Examination Report to Application No. GB 030086.6, Dec. 1, 2003.
Examination Report to Application No. GB 0306046.4, Sep. 10, 2004.
Search and Examination Report to Application No. GB 0308290.6, Jun. 2, 2003.
Search and Examination Report to Application No. GB 0308293.0, Jun. 2, 2003.
Search and Examination Report to Application No. GB 0308293.0, Jul. 14, 2003.
Search and Examination Report to Application No. GB 0308294.8, Jun. 2, 2003.
Search and Examination Report to Application No. GB 0308294.8, Jul. 14, 2003.
Search and Examination Report to Application No. GB 0308295.5, Jun. 2, 2003.

Search and Examination Report to Application No. GB 0308295.5, Jul. 14, 2003.
Search and Examination Report to Application No. GB 0308296.3, Jun. 2, 2003.
Search and Examination Report to Application No. GB 0308296.3, Jul. 14, 2003.
Search and Examination Report to Application No. GB 0308297.1, Jun. 2, 2003.
Search and Examination Report to Application No. GB 0308297.1, Jul. 2003.
Search and Examination Report to Application No. GB 0308299.7, Jun. 2, 2003.
Search and Examination Report to Application No. GB 0308299.7, Jun. 14, 2003.
Search and Examination Report to Application No. GB 0308302.9, Jun. 2, 2003.
Search and Examination Report to Application No. GB 0308303.7, Jun. 2, 2003.
Search and Examination Report to Application No. GB 0308303.7, Jul. 14, 2003.
Search and Examination Report to Application No. GB 0310090.6, Jun. 24, 2003.
Search and Examination Report to Application No. GB 0310099.7, Jun. 24, 2003.
Search and Examination Report to Application No. GB 0310101.1, Jun. 24, 2003.
Search and Examination Report to Application No. GB 0310104.5, Jun. 24, 2003.
Search and Examination Report to Application No. GB 0310118.5, Jun. 24, 2003.
Search and Examination Report to Application No. GB 0310757.0, Jun. 12, 2003.
Search and Examination Report to Application No. GB 0310759.6, Jun. 12, 2003.
Search and Examination Report to Application No. GB 0310770.3, Jun. 12, 2003.
Search and Examination Report to Application No. GB 0310772.9, Jun. 12, 2003.
Search and Examination Report to Application No. GB 0310785.1, Jun. 12, 2003.
Search and Examination Report to Application No. GB 0310795.0, Jun. 12, 2003.
Search and Examination Report to Application No. GB 0310797.6, Jun. 12, 2003.
Search and Examination Report to Application No. GB 0310799.2, Jun. 12, 2003.
Search and Examination Report to Application No. GB 0310801.6, Jun. 12, 2003.
Search and Examination Report to Application No. GB 0310833.9, Jun. 12, 2003.
Search and Examination Report to Application No. GB 0310836.2, Jun. 12, 2003.
Examination Report to Application No. GB 0310836.2, Aug. 7, 2003.
Examination Report to Application No. GB 0311596.1, May 18, 2004.
Search and Examination Report to Application No. GB 0313406.1, Sep. 3, 2003.
Search and Examination Report to Application No. GB 0313406.1, Sep. 3, 2003.
Examination Report to Application No. GB 0314846.7, Jul. 15, 2004.
Search and Examination Report to Application No. GB 0316883.8, Aug. 14, 2003.
Search and Examination Report to Application No. GB 0316883.8, Nov. 25, 2003.
Search and Examination Report to Application No. GB 0316886.1, Aug. 14, 2003.
Search and Examination Report to Application No. GB 0316886.1, Nov. 25, 2003.
Search and Examination Report to Application No. GB 0316887.9, Aug. 14, 2003.
Search and Examination Report to Application No. GB 0316887.9, Nov. 25, 2003.
Search and Examination Report to Application No. GB 0318545.1, Sep. 3, 2003.
Search and Examination Report to Application No. GB 0318547.4; Sep. 3, 2003.
Search and Examination Report to Application No. GB 0318549.3; Sep. 3, 2003.
Search and Examination Report to Application No. GB 0318550.1, Sep. 3, 2003.
Search and Examination Report to Application No. GB 0320579.6, Dec. 16, 2003.
Search and Examination Report to Application No. GB 0320580.4, Dec. 17, 2003.
Examination Report to Application No. GB 0320747.9, May 25, 2004.
Search and Examination Report to Application No. GB 0323891.2, Dec. 19, 2003.
Search and Examination Report to Application No. GB 0324172.6, Nov. 4, 2003.
Search and Examination Report to Application No. GB 0324174.2, Nov. 4, 2003.
Search and Examination Report to Application No. GB 0325071.9, Nov. 18, 2003.
Examination Report to Application No. GB 0325071.9, Feb. 2, 2004.
Examination Report to Application No. GB 0325072.7, Feb. 5, 2004.
Search and Examination Report to Application No. GB 0325072.7; Dec. 3, 2003.
Examination Report to Application No. GB 0325072.7; Apr. 13, 2004.
Examination Report to Application No. GB 0400018.8; Oct. 29, 2004.
Examination Report to Application No. GB 0400019.6; Oct. 29, 2004.
Search and Examination Report to Application No. GB 0403891.5, Jun. 9, 2004.
Examination Report to Application No. GB 0403891.5, Feb. 14, 2005.
Search and Examination Report to Application No. GB 0403893.1, Jun. 9, 2004.
Examination Report to Application No. GB 0403893.1, Feb. 14, 2005.
Search and Examination Report to Application No. GB 0403894.9, Jun. 9, 2004.
Examination Report to Application No. GB 0403894.9, Feb. 15, 2005.
Search and Examination Report to Application No. GB 0403897.2, Jun. 9, 2004.
Search and Examination Report to Application No. GB 0403920.2, Jun. 10, 2004.
Examination Report to Application No. GB 0403920.2, Feb. 15, 2005.
Search and Examination Report to Application No. GB 0403921.0, Jun. 10, 2004.
Examination Report to Application No. GB 0403921.0, Feb. 15, 2005.
Search and Examination Report to Application No. GB 0403926.9, Jun. 10, 2004.
Examination Report to Application No. GB 0404796.5; May 20, 2004.
Search and Examination Report to Application No. GB 0404826.0, Apr. 21, 2004.
Search and Examination Report to Application No. GB 0404828.6, Apr. 21, 2004.
Search and Examination Report to Application No. GB 0404830.2, Apr. 21, 2004.
Search and Examination Report to Application No. GB 0404832.8, Apr. 21, 2004.
Search and Examination Report to Application No. GB 0404833.6, Apr. 21, 2004.
Search and Examination Report to Application No. GB 0404833.6, Aug. 19, 2004.
Search and Examination Report to Application No. GB 0404837,7, May 17, 2004.
Examination Report to Application No. GB 0404837.7, Jul. 12, 2004.

Search and Examination Report to Application No. GB 0404839.3, May 14, 2004.
Search and Examination Report to Application No. GB 0404842.7, May 14, 2004.
Search and Examination Report to Application No. GB 0404845.0, May 14, 2004.
Search and Examination Report to Application No. GB 0404849.2, May 17, 2004.
Examination Report to Application No. GB 0406257.6, Jun. 28, 2004.
Examination Report to Application No. GB 0406257.6, Jan. 25, 2005.
Examination Report to Application No. GB 0406258.4, May 20, 2004.
Examination Report to Application No. GB 0406258.4; Jan. 12, 2005.
Examination Report to Application No. GB 0408672.4, Jul. 12, 2004.
Examination Report to Application No. GB 0408672.4, Mar. 21, 2005.
Examination Report to Application No. GB 0404830.2, Aug. 17, 2004.
Search and Examination Report to Application No. GB 0411698.4, Jun. 30, 2004.
Examination Report to Application No. GB 0411698.4, Jan. 24, 2005.
Search and Examination Report to Application No. GB 0411892.3, Jul. 14, 2004.
Examination Report to Application No. GB 0411892.3, Feb. 21, 2005.
Search and Examination Report to Application No. GB 0411893.3, Jul. 14, 2004.
Search and Examination Report to Application No. GB 0411894.9, Jun. 30, 2004.
Search and Examination Report to Application No. GB 0412190.1, Jul. 22, 2004.
Search and Examination Report to Application No. GB 0412191.9, Jul. 22, 2004.
Search and Examination Report to Application No. GB 0412192.7, Jul. 22, 2004.
Search Report to Application No. GB 0415835.8, Dec. 2, 2004.
Search Report to Application No. GB 0415835.8; Mar. 10, 2005.
Examination Report to Application No. 0416625.2 Jan. 20, 2005.
Search and Examination Report to Application No. GB 0416834.0, Aug. 11, 2004.
Search and Examination Report to Application No. GB 0416834.0, Nov. 16, 2004.
Search and Examination Report to Application No. GB 0417810.9, Aug. 25, 2004.
Search and Examination Report to Application No. GB 0417811.7, Aug. 25, 2004.
Search and Examination Report to Application No. GB 0418005.5, Aug. 25, 2004.
Search and Examination Report to Application No. GB 0418425.5, Sep. 10, 2004.
Search and Examination Report to Application No. GB 0418426.3 Sep. 10, 2004.
Search and Examination Report to Application No. GB 0418427.1 Sep. 10, 2004.
Search and Examination Report to Application No. GB 0418429.7 Sep. 10, 2004.
Search and Examination Report to Application No. GB 0418430.5 Sep. 10, 2004.
Search and Examination Report to Application No. GB 0418431.3 Sep. 10, 2004.
Search and Examination Report to Application No. GB 0418432.1 Sep. 10, 2004.
Search and Examination Report to Application No. GB 0418433.9 Sep. 10, 2004.
Search and Examination Report to Application No. GB 0418439.6 Sep. 10, 2004.
Search and Examination Report to Application No. GB 0418442.0 Sep. 10, 2004.
Examination Report to Application No. GB 0422419.2 Dec. 8, 2004.
Search and Examination Report to Application No. GB 0422893.8 Nov. 24, 2004.
Search and Examination Report to Application No. GB 0423416.7 Nov. 12, 2004.
Search and Examination Report to Application No. GB 0423417.5 Nov. 12, 2004.
Search and Examination Report to Application No. GB 0423418.3 Nov. 12, 2004.
Search and Examination Report to Application No. GB 0426155.8 Jan. 12, 2005.
Search and Examination Report to Application No. GB 0426156.6 Jan. 12, 2005.
Search and Examination Report to Application No. GB 0426157.4 Jan. 12, 2005.
Examination Report to Application No. GB 0428141.6 Feb. 9, 2005.
Examination Report to Application No. GB 0500184.7 Feb. 9, 2005.
Search and Examination Report to Application No. GB 0500600.2 Feb. 15, 2005.
Search and Examination Report to Application No. GB 0503470.7 Mar. 21, 2005.
Search Report to Application No. GB 9926449.1, Mar. 27, 2000.
Search Report to Application No. GB 9926449.1, Jul. 4, 2001.
Search Report to Application No. GB 9926449.1, Sep. 5, 2001.
Search Report to Application No. GB 9926450.9, Feb. 28, 2000.
Examination Report to Application No. GB 9926450.9, May 15, 2002.
Examination Report to Application No. GB 9926450.9, Nov. 22, 2002.
Search Report to Application No. GB 9930398.4, Jun. 27, 2000.
Search Report to Application No. Norway 1999 5593, Aug. 20, 2002.
Written Opinion to Application No. PCT/US01/19014; Dec. 10, 2002.
Written Opinion to Application No. PCT/US01/23815; Jul. 25, 2002.
Written Opinion to Application No. PCT/US01/28960; Dec. 2, 2002.
Written Opinion to Application No. PCT/US01/30256; Nov. 11, 2002.
Written Opinion to Application No. PCT/US02/00093; Apr. 21, 2003.
Written Opinion to Application No. PCT/US02/00677; Apr. 17, 2003.
Written Opinion to Application No. PCT/US02/04353; Apr. 11, 2003.
Written Opinion to Application No. PCT/US02/20256; May 9, 2003.
Written Opinion to Application No. PCT/US02/24399; Apr. 28, 2004.
Written Opinion to Application No. PCT/US02/25608 Sep. 13, 2004.
Written Opinion to Application No. PCT/US02/25608 Feb. 2, 2005.
Written Opinion to Application No. PCT/US03/25675 Nov. 24, 2004.
Written Opinion to Application No. PCT/US02/25727; May 17, 2004.
Written Opinion to Application No. PCT/US02/39418; Jun. 9, 2004.
Written Opinion to Application No. PCT/US02/39425; Nov. 22, 2004.
iWritten Opinion to Application No. PCT/US02/39425; Apr. 11, 2005.
Written Opinion to Application No. PCT/US03/06544; Feb. 18, 2005.
Written Opinion to Application No. PCT/US03/11765 May 11, 2004.
Written Opinion to Application No. PCT/US03/13787 Nov. 9, 2004.
Written Opinion to Application No. PCT/US03/14153 Sep. 9, 2004.
Written Opinion to Application No. PCT/US03/14153 Nov. 9, 2004.
Written Opinion to Application No. PCT/US03/18530 Sep. 13, 2004.
Written Opinion to Application No. PCT/US03/19993 Oct. 15, 2004.
Written Opinion to Application No. PCT/US03/29858 Jan. 21, 2004.
Written Opinion to Application No. PCT/US03/38550 Dec. 10, 2004.
Written Opinion to Application No. PCT/US04/08171 May 5, 2005.
Combined Search Report and Written Opinion to Application No. PCT/US04/00631; Mar. 28, 2005.
Combined Search Report and Written Opinion to Application No. PCT/US04/02122 Feb. 24, 2005.
Combined Search Report and Written Opinion to Application No. PCT/US04/04740 Jan. 19, 2005.

Combined Search Report and Written Opinion to Application No. PCT/US04/06246 Jan. 26, 2005.
Combined Search Report and Written Opinion to Application No. PCT/US04/08030 Jan. 6, 2005.
Combined Search Report and Written Opinion to Application No. PCT/US04/08073 Mar. 4, 2005.
Combined Search Report and Written Opinion to Application No. PCT/US04/08170 Jan. 13, 2005.
Combined Search Report and Written Opinion to Application No. PCT/US04/08171 Feb. 16, 2005.
Combined Search Report and Written Opinion to Application No. PCT/US04/11172 Feb. 14, 2005.
Combined Search Report and Written Opinion to Application No. PCT/US04/28438 Mar. 14, 2005.

* cited by examiner

PIPE FORMABILITY EVALUATION FOR EXPANDABLE TUBULARS

CROSS REFERENCE TO RELATED APPLICATIONS

The present application is the National Stage patent application for PCT patent application Ser. No. PCT/US2003/025667, filed on Aug. 18, 2003, which claimed the benefit of the filing dates of (1) U.S. provisional patent application Ser. No. 60/412,653, filed on Sep. 20, 2002, the disclosures of which are incorporated herein by reference.

The present application is related to the following: (1) U.S. patent application Ser. No. 09/454,139, filed on Dec. 3, 1999, (2) U.S. patent application Ser. No. 09/510,913, filed on Feb. 23, 2000, (3) U.S. patent application Ser. No. 09/502,350, filed on Feb. 10, 2000, (4) U.S. Pat. No. 6,328,113, (5) U.S. patent application Ser. No. 09/523,460, filed on Mar. 10, 2000, (6) U.S. patent application Ser. No. 09/512,895, filed on Feb. 24, 2000, (7) U.S. patent application Ser. No. 09/511,941, filed on Feb. 24, 2000, (8) U.S. patent application Ser. No. 09/588,946, filed on Jun. 7, 2000, (9) U.S. patent application Ser. No. 09/559,122, filed on Apr. 26, 2000, (10) PCT patent application Ser. No. PCT/US00/18635, filed on Jul. 9, 2000, (11) U.S. provisional patent application Ser. No. 60/162,671, filed on Nov. 1, 1999, (12) U.S. provisional patent application Ser. No. 60/154,047, filed on Sep. 16, 1999, (13) U.S. provisional patent application Ser. No. 60/159,082, filed on Oct. 12, 1999, (14) U.S. provisional patent application Ser. No. 60/159,039, filed on Oct. 12, 1999, (15) U.S. provisional patent application Ser. No. 60/159,033, filed on Oct. 12, 1999, (16) U.S. provisional patent application Ser. No. 60/212,359, filed on Jun. 19, 2000, (17) U.S. provisional patent application Ser. No. 60/165,228, filed on Nov. 12, 1999, (18) U.S. provisional patent application Ser. No. 60/221,443, filed on Jul. 28, 2000, (19) U.S. provisional patent application Ser. No. 60/221,645, filed on Jul. 28, 2000, (20) U.S. provisional patent application Ser. No. 60/233,638, on Sep. 18, 2000, (21) U.S. provisional patent application Ser. No. 60/237,334, filed on Oct. 2, 2000, (22) U.S. provisional patent application Ser. No. 60/270,007, filed on Feb. 20, 2001, (23) U.S. provisional patent application Ser. No. 60/262,434, filed on Jan. 17, 2001, (24) U.S. provisional patent application Ser. No. 60/259,486, filed on Jan. 3, 2001, (25) U.S. provisional patent application Ser. No. 60/303,740, filed on Jul. 6, 2001, (26) U.S. provisional patent application Ser. No. 60/313,453, filed on Aug. 20, 2001, (27) U.S. provisional patent application Ser. No. 60/317,985, filed on Sep. 6, 2001, (28) U.S. provisional patent application Ser. No. 60/3318,386, filed on Sep. 10, 2001, (29) U.S. utility patent application Ser. No. 09/969,922, filed on Oct. 3, 2001, (30) U.S. utility patent application Ser. No. 10/016,467, filed on Dec. 10, 2001, (31) U.S. provisional patent application Ser. No. 60/343,674, filed on Dec. 27, 2001, (32) U.S. provisional patent application Ser. No. 60/346,309, filed on Jan. 7, 2002, (33) U.S. provisional patent application Ser. No. 60/372,048, filed on Apr. 12, 2002, (34) U.S. provisional patent application Ser. No. 60/380,147, filed on May 6, 2002, (35) U.S. provisional patent application Ser. No. 60/387,486, filed on Jun. 10, 2002, (36) U.S. provisional patent application Ser. No. 60/387,961, filed on Jun. 12, 2002, (37) U.S. provisional patent application Ser. No. 60/394,703, filed on Jun. 26, 2002, (38) U.S. provisional patent application Ser. No. 60/397,284, filed on Jul. 19, 2002, (39) U.S. provisional patent application Ser. No. 60/398,061, filed on Jul. 24, 2002, (40) U.S. provisional patent application Ser. No, 60/405,610, filed on Aug. 23, 2002, (41) U.S. provisional patent application Ser. No. 60/405,394, filed on Aug. 23, 2002, (42) U.S. provisional patent application Ser. No. 60/412,542, filed on Sep. 20, 2002, (43) U.S. provisional patent application Ser. No. 60/412,487, filed on Sep. 20, 2002, (44) U.S. provisional patent application Ser. No. 60/412,488, filed on Sep. 20, 2002, (45) U.S. provisional patent application Ser. No. 60/412,177, filed on Sep. 20, 2002, (46) U.S. provisional patent application Ser. No. 60/412,653, filed on Sep. 20, 2002, (47) U.S. provisional patent application Ser. No. 60/412,544, filed on Sep. 20, 2002, (48) U.S. provisional patent application Ser. No. 60/412,196, filed on Sep. 20, 2002, (49) U.S. provisional patent application Ser. No. 60/412,187, filed on Sep. 20, 2002, and (50) U.S. provisional patent application Ser. No. 60/412,371, filed on Sep. 20, 2002, the disclosures of which are incorporated herein by reference.

The present application is related to each of the following: (1) U.S. utility patent application Ser. No. 60/412,544, filed on Sep. 23, 2002; and (2) U.S. utility patent application Ser. No. 60/412,371, filed on Sep. 20, 2002.

BACKGROUND OF THE INVENTION

The present invention relates generally to tubular steel well casing and more particularly to an expansion mandrel which reduces stress during expansion of the casing.

Solid tubular casing of substantial length is used as a borehole liner in downhole drilling. The casing is comprised of end-to-end interconnected segments of steel tubing to protect against possible collapse of the borehole and to optimize well flow. The tubing often reaches substantial depths and endures substantial pressures.

It is present practice to expand the steel tubing downhole by using a mandrel. This is a cold-working process which presents substantial mechanical challenges. This technology is known as solid expandable tubular (SET) technology. This cold-working process deforms the steel without any additional heat beyond what is present in the downhole environment.

An expansion cone, or mandrel, is used to permanently mechanically deform the pipe. The cone is moved through the tubing by a differential hydraulic pressure across the cone itself, and/or by a direct mechanical pull or push force. The differential pressure is pumped through an inner-string connected to the cone, and the mechanical force is applied by either raising or lowering the inner string.

Progress of the cone through the tubing deforms the steel beyond its elastic limit into the plastic region, while keeping stresses below ultimate yield. Expansions greater than 20%, based on pipe ID, have been accomplished. However, most applications using 4¼-13⅜ inch tubing have required expansions less than 20%. The ID of the pipe expands to the same ID of the expansion mandrel, which is a function of expansion mandrel OD. Contact between cylindrical mandrel and pipe ID during expansion leads to significant forces due to friction. It would be beneficial to provide method for testing tubular members for suitability for the expansion process. It would also be beneficial to provide a method for selecting tubing or tubular members well suited for expansion.

SUMMARY OF THE INVENTION

According to one aspect of the present invention, a method of testing a tubular member for suitability for expansion is provided using an expandability coefficient determined pursuant to a stress-strain test of a tubular member using axial loading.

According to another aspect of the present invention, a tubular member is selected for suitability for expansion on a basis comprising use of an expandability coefficient determined pursuant to a stress-strain test of a tubular member using axial loading.

According to another aspect of the present invention, a method of testing a tubular member for suitability for expansion is provided using an expandability coefficient determined pursuant to a stress-strain test using axial loading comprising calculation of plastic strain ratio for obtaining the expansion coefficient pursuant to test results and using the formula:

$$f = \frac{\ln\frac{b_o}{b_k}}{\ln\frac{L_k b_k}{L_o b_o}} \qquad \text{Equation 1}$$

where, f—expandability coefficient bo & bk—initial and final tube area (inch^2)

Lo & Lk—initial and final tube length (inch)

b=(D^2−d^2)/4—cross section tube area.

According to another aspect of the present invention, a tubular member is selected for suitability for expansion on a basis comprising use of an expandability coefficient determined pursuant to a stress-strain test using axial loading comprising calculation of plastic strain ratio for obtaining the expansion coefficient pursuant to test results and using the formula:

$$f = \frac{\ln\frac{b_o}{b_k}}{\ln\frac{L_k b_k}{L_o b_o}} \qquad \text{Equation 1}$$

where, f—expandability coefficient bo & bk—initial and final tube area (inch^2)

Lo & Lk—initial and final tube length (inch)

b=(D^2−d^2)/4—cross section tube area.

According to another aspect of the present invention, a tubular member is selected for suitability for expansion on a basis comprising use of an expandability coefficient determined pursuant to a stress-strain test using axial loading and one or more physical properties of the tubular member selected from stress-strain properties in one or more directional orientations of the material, Charpy V-notch impact value in one or more directional orientations of the material, stress rupture burst strength, stress rupture collapse strength, strain-hardening exponent (n-value), hardness and yield strength.

According to another aspect of the present invention, a method for manufacturing an expandable member used to complete a structure by radially expanding and plastically deforming the expandable member is provided that includes forming the expandable member from a steel alloy comprising a charpy energy of at least about 90 ft-lbs.

According to another aspect of the present invention, an expandable member for use in completing a structure by radially expanding and plastically deforming the expandable member is provided that includes a steel alloy comprising a charpy energy of at least about 90 ft-lbs.

According to another aspect of the present invention, a structural completion positioned within a structure is provided that includes one or more radially expanded and plastically deformed expandable members positioned within the structure; wherein one or more of the radially expanded and plastically deformed expandable members are fabricated from a steel alloy comprising a charpy energy of at least about 90 ft-lbs.

According to another aspect of the present invention, a method for manufacturing an expandable member used to complete a structure by radially expanding and plastically deforming the expandable member is provided that includes forming the expandable member from a steel alloy comprising a weight percentage of carbon of less than about 0.08%.

According to another aspect of the present invention, an expandable member for use in completing a wellbore by radially expanding and plastically deforming the expandable member at a downhole location in the wellbore is provided that includes a steel alloy comprising a weight percentage of carbon of less than about 0.08%.

According to another aspect of the present invention, a structural completion is provided that includes one or more radially expanded and plastically deformed expandable members positioned within the wellbore; wherein one or more of the radially expanded and plastically deformed expandable members are fabricated from a steel alloy comprising a weight percentage of carbon of less than about 0.08%.

According to another aspect of the present invention, a method for manufacturing an expandable member used to complete a structure by radially expanding and plastically deforming the expandable member is provided that includes forming the expandable member from a steel alloy comprising a weight percentage of carbon of less than about 0.20% and a charpy V-notch impact toughness of at least about 6 joules.

According to another aspect of the present invention, an expandable member for use in completing a structure by radially expanding and plastically deforming the expandable member is provided that includes a steel alloy comprising a weight percentage of carbon of less than about 0.20% and a charpy V-notch impact toughness of at least about 6 joules.

According to another aspect of the present invention, a structural completion is provided that includes one or more radially expanded and plastically deformed expandable members; wherein one or more of the radially expanded and plastically deformed expandable members are fabricated from a steel alloy comprising a weight percentage of carbon of less than about 0.20% and a charpy V-notch impact toughness of at least about 6 joules.

According to another aspect of the present invention, a method for manufacturing an expandable member used to complete a structure by radially expanding and plastically deforming the expandable member is provided that includes forming the expandable member from a steel alloy comprising the following ranges of weight percentages: C, from about 0.002 to about 0.08; Si, from about 0.009 to about 0.30; Mn, from about 0.10 to about 1.92; P, from about 0.004 to about 0.07; S, from about 0.0008 to about 0.006; Al, up to about 0.04; N, up to about 0.01; Cu, up to about 0.3; Cr, up to about 0.5; Ni, up to about 18; Nb, up to about 0.12; Ti, up to about 0.6; Co, up to about 9; and Mo, up to about 5.

According to another aspect of the present invention, an expandable member for use in completing a structure by radially expanding and plastically deforming the expandable member is provided that includes a steel alloy comprising the following ranges of weight percentages: C, from about 0.002 to about 0.08; Si, from about 0.009 to about 0.30; Mn, from about 0.10 to about 1.92; P, from about 0.004 to about 0.07; S, from about 0.0008 to about 0.006; Al, up to about 0.04; N, up to about 0.01; Cu, up to about 0.3; Cr, up to about 0.5; Ni, up to about 18; Nb, up to about 0.12; Ti, up to about 0.6; Co, up to about 9; and Db, up to about 5.

According to another aspect of the present invention, a structural completion is provided that includes one or more radially expanded and plastically deformed expandable members; wherein one or more of the radially expanded and plastically deformed expandable members are fabricated from a steel alloy comprising the following ranges of weight percentages: C, from about 0.002 to about 0.08; Si, from about 0.009 to about 0.30; Mn, from about 0.10 to about 1.92; P, from about 0.004 to about 0.07; S, from about 0.0008 to about 0.006; Al, up to about 0.04; N, up to about 0.01; Cu, up to about 0.3; Cr, up to about 0.5; Ni, up to about 18; Nb, up to about 0.12; Ti, up to about 0.6; Co, up to about 9; and Mo, up to about 5.

According to another aspect of the present invention, a method for manufacturing an expandable tubular member used to complete a structure by radially expanding and plastically deforming the expandable member is provided that includes forming the expandable tubular member with a ratio of the of an outside diameter of the expandable tubular member to a wall thickness of the expandable tubular member ranging from about 12 to 22.

According to another aspect of the present invention, an expandable member for use in completing a structure by radially expanding and plastically deforming the expandable member is provided that includes an expandable tubular member with a ratio of the of an outside diameter of the expandable tubular member to a wall thickness of the expandable tubular member ranging from about 12 to 22.

According to another aspect of the present invention, a structural completion is provided that includes one or more radially expanded and plastically deformed expandable members positioned within the structure; wherein one or more of the radially expanded and plastically deformed expandable members are fabricated from an expandable tubular member with a ratio of the of an outside diameter of the expandable tubular member to a wall thickness of the expandable tubular member ranging from about 12 to 22.

According to another aspect of the present invention, a method of constructing a structure is provided that includes radially expanding and plastically deforming an expandable member; wherein an outer portion of the wall thickness of the radially expanded and plastically deformed expandable member comprises tensile residual stresses.

According to another aspect of the present invention, a structural completion is provided that includes one or more radially expanded and plastically deformed expandable members; wherein an outer portion of the wall thickness of one or more of the radially expanded and plastically deformed expandable members comprises tensile residual stresses.

According to another aspect of the present invention, a method of constructing a structure using an expandable tubular member is provided that includes strain aging the expandable member; and then radially expanding and plastically deforming the expandable member.

According to another aspect of the present invention, a method for manufacturing a tubular member used to complete a wellbore by radially expanding the tubular member at a downhole location in the wellbore comprising: forming a steel alloy comprising a concentration of carbon between approximately 0.002% and 0.08% by weight of the steel alloy.

DETAILED DESCRIPTION OF THE ILLUSTRATIVE EMBODIMENTS

Figure 1:
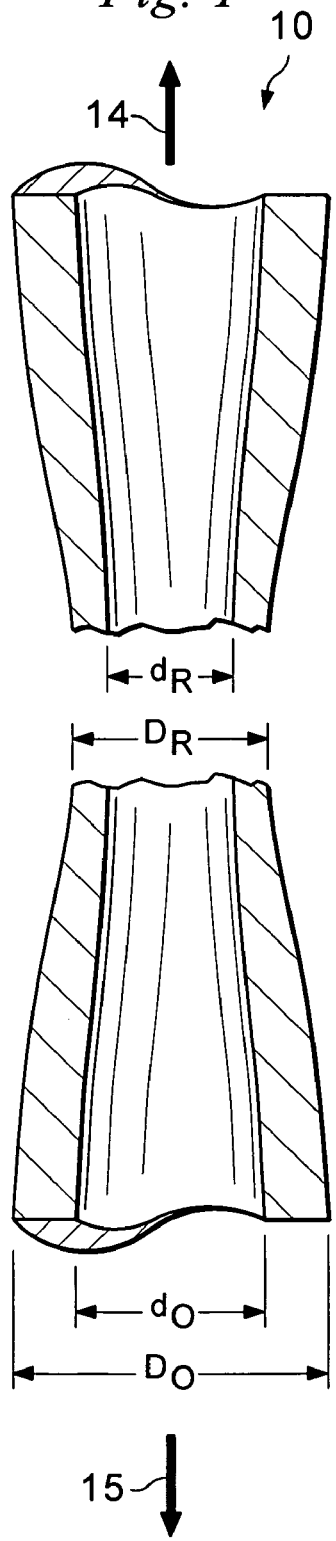
FIG. 1 depicts in a schematic fragmentary cross-sectional view along a plane along and through the central axis of a tubular member that is tested to failure with axial opposed forces.

One of the problems of the pipe material selection for expandable tubular application is an apparent contradiction or inconsistency between strength and elongation. To increase burst and collapse strength, material with higher yield strength is used. The higher yield strength generally corresponds to a decrease in the fracture toughness and correspondingly limits the extent of achievable expansion.

It is desirable to select the steel material for the tubing by balancing steel strength with amount absorbed energy measure by Charpy testing. Generally these tests are done on samples cut from tubular members. It has been found to be beneficial to cut directional samples both longitudinally oriented (aligned with the axis) and circumferentially oriented (generally perpendicular to the axis). This method of selecting samples is beneficial when both directional orientations are used yet does not completely evaluate possible and characteristic anisotropy throughout a tubular member. Moreover, for small diameter tubing samples representative of the circumferential direction may be difficult and sometimes impossible to obtain because of the significant curvature of the tubing.

To further facilitate evaluation of a tubular member for suitability for expansion it has been found beneficial according to one aspect of the invention to consider the plastic strain ratio. One such ratio is called a Lankford value (or r-value) which is the ratio of the strains occurring in the width and thickness directions measured in a single tension test. The plastic strain ratio (r or Lankford-value) with a value of greater than 1.0 is found to be more resistant to thinning and better suited to tubular expansion. Such a Lankford value is found to be a measure of plastic anisotropy. The Lankford value (r) may be calculate by the Equation 2 below.

$$r = \frac{\ln\frac{b_o}{b_k}}{\ln\frac{L_k b_k}{L_o b_o}} \qquad \text{Equation 2}$$

where, r—normal anisotropy coefficient bo & bk—initial and final width

Lo & Lk—initial and final length

However, it is time consuming and labor intensive for this parameter to be measured using samples cut from real parts such as from the tubular members. The tubular members will have anisotropic characteristics due to crystallographic or "grain" orientation and mechanically induced differences such as impurities, inclusions, and voids, requiring multiple samples for reliably complete information. Moreover, with individual samples, only local characteristics are determined and the complete anisotropy of the tubular member may not be determinable. Further some of the tubular members have small diameters so that cutting samples oriented in a circumferential direction is not always possible. Information regarding the characteristics in the circumferential direction has been found to be important because the plastic deformation during expansion of the tubular members occurs to a very large extent in the circumferential direction, One aspect of the present invention comprises the development of a solution for anisotropy evaluation, including a kind of plastic strain ratio similar to the Lankford parameter that is measured using real tubular members subjected to axial loading.

FIG. 1 depicts in a schematic fragmentary cross-sectional view along a plane along and through the axis 12 of a tubular member 10 that is tested with axial opposed forces 14 and 15. The tubular member 10 is axially stretched beyond the elastic limit, through yielding and to ultimate yield or fracture. Measurements of the force and the OD and ID during the process produce test data that can be used in the formula below to produce an expandability coefficient "f" as set forth in Equation 1 above. Alternatively a coefficient called a formability anisotropy coefficient F(r) that is function of the normal anisotropy Lankford coefficient r may be determined as in Equation 3 below.

$$F(r) = \frac{\ln\frac{b_o}{b_k}}{\ln\frac{L_k b_k}{L_o b_o}} \quad \text{Equation 3}$$

F(r)—formability anisotropy coefficient f—expandability coefficient bo & bk—initial and final tube area (inch^2)

Lo & Lk—initial and final tube length (inch)

b=(D^2−d^2)/4—cross section tube area.

In either circumstance f or F(r) the use of this testing method for an entire tubular member provides useful information including anisotropic characteristics or anisotropy of the tubular member for selecting or producing beneficial tubular members for down hole expansion, similar to the use of the Lankford value for a sheet material.

Figure 2:
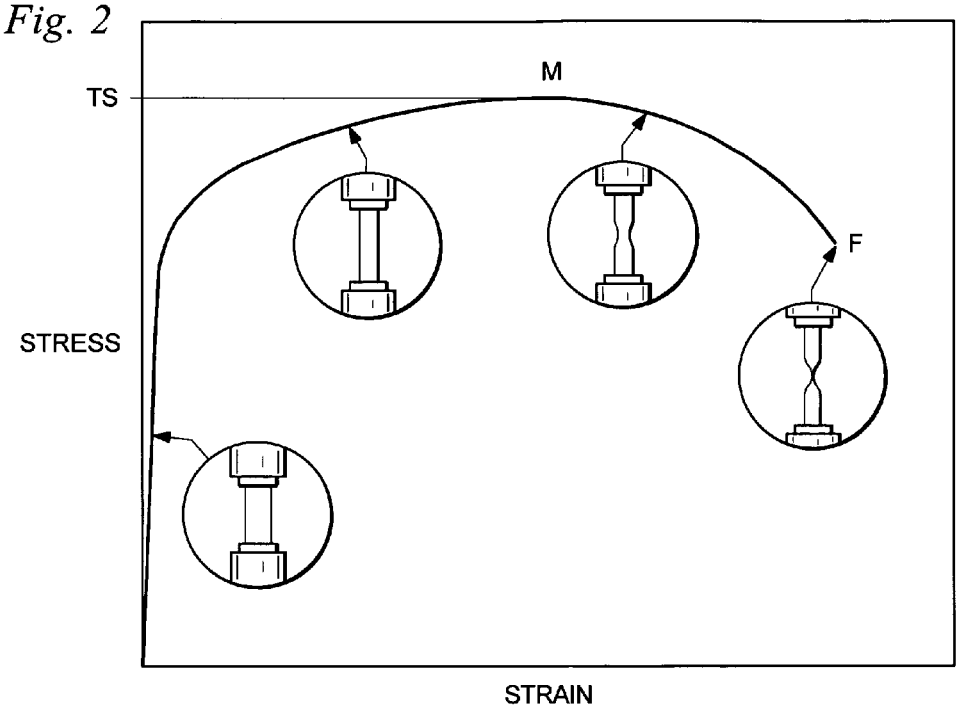
FIG. 2 is a stress-strain curve representing values for stress and strain that may be plotted for solid specimen sample.
Figure 3:
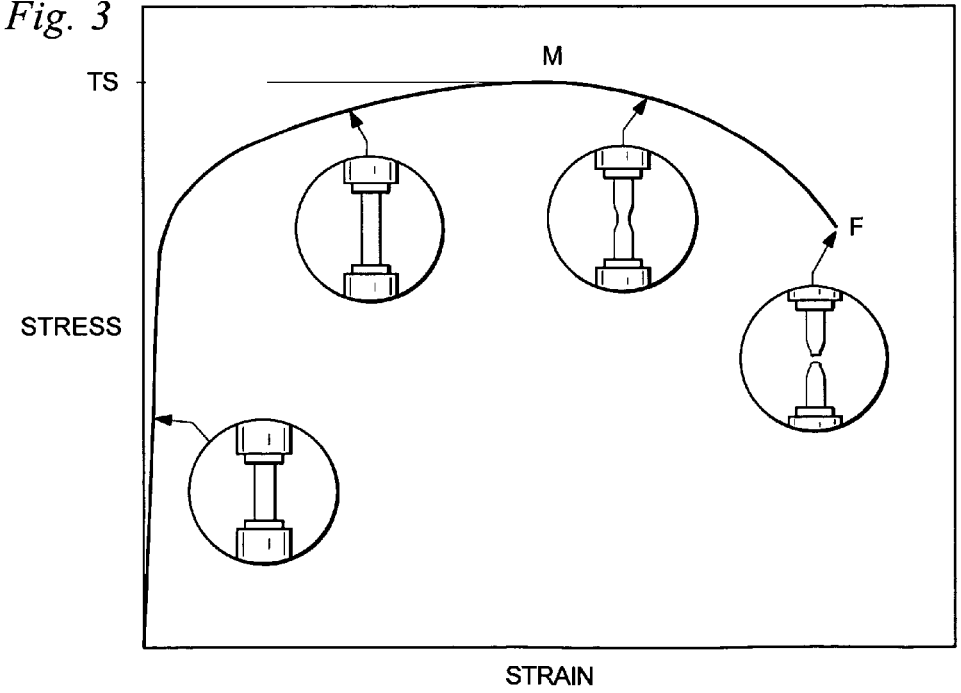
FIG. 3. is a schematically depiction of a stress strain curve representing values from a test on a tubular member according to an illustrative example of one aspect of the invention.

Just as values for stress and strain may be plotted for solid specimen samples, as schematically depicted in FIG. 2, the values for conducting a test on the tubular member may also be plotted, as depicted in FIG. 3. On this basis the expansion coefficient f (or the formability coefficient F(r)) may be determined. It will be the best to measure distribution (Tensile-elongation) in longitudinal and circumferential directions simultaneously.

The foregoing expandability coefficient (or formability coefficient) is found to be useful in predicting good expansion results and may be further useful when used in combination with one or more other properties of a tubular member selected from stress-strain properties in one or more directional orientations of the material, strength & elongation, Charpy V-notch impact value in one or more directional orientations of the material, stress burst rupture, stress collapse rupture, yield strength, ductility, toughness, and strain-hardening exponent (n-value), and hardness.

In an exemplary embodiment, a tribological system is used to reduce friction and thereby minimize the expansion forces required during the radial expansion and plastic deformation of the tubular members that includes one or more of the following: (1) a tubular tribology system; (2) a drilling mud tribology system; (3) a lubrication tribology system; and (4) an expansion device tribology system.

In an exemplary embodiment, the tubular tribology system includes the application of coatings of lubricant to the interior surface of the tubular members.

In an exemplary embodiment, the drilling mud tribology system includes the addition of lubricating additives to the drilling mud.

In an exemplary embodiment, the lubrication tribology system includes the use of lubricating greases, self-lubricating expansion devices, automated injection/delivery of lubricating greases into the interface between an expansion device and the tubular members, surfaces within the interface between the expansion device and the expandable tubular member that are self-lubricating, surfaces within the interface between the expansion device and the expandable tubular member that are textured, self-lubricating surfaces within the interface between the expansion device and the expandable tubular member that include diamond and/or ceramic inserts, thermosprayed coatings, fluoropolymer coatings, PVD films, and/or CVD films.

In an exemplary embodiment, the tubular members include one or more of the following characteristics: high burst and collapse, the ability to be radially expanded more than about40%, high fracture toughness, defect tolerance, strain recovery @ 150 F, good bending fatigue, optimal residual stresses, and corrosion resistance to $H_2S$ in order to provide optimal characteristics during and after radial expansion and plastic deformation.

In an exemplary embodiment, the tubular members are fabricated from a steel alloy having a charpy energy of at least about 90 ft-lbs in order to provided enhanced characteristics during and after radial expansion and plastic deformation of the expandable tubular member.

In an exemplary embodiment, the tubular members are fabricated from a steel alloy having a weight percentage of carbon of less than about 0.08% in order to provide enhanced characteristics during and after radial expansion and plastic deformation of the tubular members.

In an exemplary embodiment, the tubular members are fabricated from a steel alloy having reduced sulfur content in order to minimize hydrogen induced cracking.

In an exemplary embodiment, the tubular members are fabricated from a steel alloy having a weight percentage of carbon of less than about 0.20% and a charpy-V-notch impact toughness of at least about 6 joules in order to provide enhanced characteristics during and after radial expansion and plastic deformation of the tubular members.

In an exemplary embodiment, the tubular members are fabricated from a steel alloy having a low weight percentage of carbon in order to enhance toughness, ductility, weldability, shelf energy, and hydrogen induced cracking resistance.

In several exemplary embodiments, the tubular members are fabricated from a steel alloy having the following percentage compositions in order to provide enhanced characteristics during and after radial expansion and plastic deformation of the tubular members:

|  | C | Si | Mn | P | S | Al | N | Cu | Cr | Ni | Nb | Ti | Co | Mo |
|---|---|---|---|---|---|---|---|---|---|---|---|---|---|---|
| EXAMPLE A | 0.030 | 0.22 | 1.74 | 0.005 | 0.0005 | 0.028 | 0.0037 | 0.30 | 0.26 | 0.15 | 0.095 | 0.014 | 0.0034 |  |
| EXAMPLE B MIN | 0.020 | 0.23 | 1.70 | 0.004 | 0.0005 | 0.026 | 0.0030 | 0.27 | 0.26 | 0.16 | 0.096 | 0.012 | 0.0021 |  |
| EXAMPLE B MAX | 0.032 | 0.26 | 1.92 | 0.009 | 0.0010 | 0.035 | 0.0047 | 0.32 | 0.29 | 0.18 | 0.120 | 0.016 | 0.0050 |  |
| EXAMPLE C | 0.028 | 0.24 | 1.77 | 0.007 | 0.0008 | 0.030 | 0.0035 | 0.29 | 0.27 | 0.17 | 0.101 | 0.014 | 0.0028 | 0.0020 |
| EXAMPLE D | 0.08 | 0.30 | 0.5 | 0.07 | 0.005 |  | 0.010 | 0.10 | 0.50 | 0.10 |  |  |  |  |
| EXAMPLE E | 0.0028 | 0.009 | 0.17 | 0.011 | 0.006 | 0.027 | 0.0029 |  | 0.029 | 0.014 | 0.035 | 0.007 |  |  |
| EXAMPLE F | 0.03 | 0.1 | 0.1 | 0.015 | 0.005 |  |  |  |  | 18.0 |  | 0.6 | 9 | 5 |
| EXAMPLE G | 0.002 | 0.01 | 0.15 | 0.07 | 0.005 | 0.04 | 0.0025 |  |  |  | 0.015 | 0.010 |  |  |

In an exemplary embodiment, the ratio of the outside diameter D of the tubular members to the wall thickness t of the tubular members range from about 12 to 22 in order to enhance the collapse strength of the radially expanded and plastically deformed tubular members.

In an exemplary embodiment, the outer portion of the wall thickness of the radially expanded and plastically deformed tubular members includes tensile residual stresses in order to enhance the collapse strength following radial expansion and plastic deformation.

In several exemplary experimental embodiments, reducing residual stresses in samples of the tubular members prior to radial expansion and plastic deformation increased the collapse strength of the radially expanded and plastically deformed tubular members.

In several exemplary experimental embodiments, the collapse strength of radially expanded and plastically deformed samples of the tubulars were determined on an as-received basis, after strain aging at 250 F for 5 hours to reduce residual stresses, and after strain aging at 350 F for 14 days to reduce residual stresses as follows:

| Tubular Sample | Collapse Strength After 10% Radial Expansion |
|---|---|
| Tubular Sample 1 - as received from manufacturer | 4000 psi |
| Tubular Sample 1 - strain aged at 250 F. for 5 hours to reduce residual stresses | 4800 psi |
| Tubular Sample 1 - strain aged at 350 F. for 14 days to reduce residual stresses | 5000 psi |

As indicated by the above table, reducing residual stresses in the tubular members, prior to radial expansion and plastic deformation, significantly increased the resulting collapse strength—post expansion.

A method for manufacturing an expandable member used to complete a structure by radially expanding and plastically deforming the expandable member has been described that includes forming the expandable member from a steel alloy comprising a charpy energy of at least about 90 ft-lbs.

An expandable member for use in completing a structure by radially expanding and plastically deforming the expandable member has been described that includes a steel alloy comprising a charpy energy of at least about 90 ft-lbs.

A structural completion positioned within a structure has been described that includes one or more radially expanded and plastically deformed expandable members positioned within the structure; wherein one or more of the radially expanded and plastically deformed expandable members are fabricated from a steel alloy comprising a charpy energy of at least about 90 ft-lbs.

A method for manufacturing an expandable member used to complete a structure by radially expanding and plastically deforming the expandable member has been described that includes forming the expandable member from a steel alloy comprising a weight percentage of carbon of less than about 0.08%.

An expandable member for use in completing a wellbore by radially expanding and plastically deforming the expandable member at a downhole location in the wellbore has been described that includes a steel alloy comprising a weight percentage of carbon of less than about 0.08%.

A structural completion has been described that includes one or more radially expanded and plastically deformed expandable members positioned within the wellbore; wherein one or more of the radially expanded and plastically deformed expandable members are fabricated from a steel alloy comprising a weight percentage of carbon of less than about 0.08%.

A method for manufacturing an expandable member used to complete a structure by radially expanding and plastically deforming the expandable member has been described that includes forming the expandable member from a steel alloy comprising a weight percentage of carbon of less than about 0.20% and a charpy V-notch impact toughness of at least about 6 joules.

An expandable member for use in completing a structure by radially expanding and plastically deforming the expandable member has been described that includes a steel alloy comprising a weight percentage of carbon of less than about 0.20% and a charpy V-notch impact toughness of at least about 6 joules.

A structural completion has been described that includes one or more radially expanded and plastically deformed expandable members; wherein one or more of the radially expanded and plastically deformed expandable members are fabricated from a steel alloy comprising a weight percentage of carbon of less than about 0.20% and a charpy V-notch impact toughness of at least about 6 joules.

A method for manufacturing an expandable member used to complete a structure by radially expanding and plastically deforming the expandable member has been described that includes forming the expandable member from a steel alloy comprising the following ranges of weight percentages: C, from about 0.002 to about 0.08; Si, from about 0.009 to about 0.30; Mn, from about 0.10 to about 1.92; P, from about 0.004 to about 0.07; S, from about 0.0008 to about 0.006; Al, up to about 0.04; N, up to about 0.01; Cu, up to about 0.3; Cr, up to about 0.5; Ni, up to about 18; Nb, up to about 0.12; Ti, up to about 0.6; Co, up to about 9; and Mo, up to about 5.

An expandable member for use in completing a structure by radially expanding and plastically deforming the expandable member has been described that includes a steel alloy comprising the following ranges of weight percentages: C, from about 0.002 to about 0.08; Si, from about 0.009 to about 0.30; Mn, from about 0.10 to about 1.92; P, from about 0.004 to about 0.07; S, from about 0.0008 to about 0.006; Al, up to about 0.04; N, up to about 0.01; Cu, up to about 0.3; Cr, up to about 0.5; Ni, up to about 18; Nb, up to about 0.12; Ti, up to about 0.6; Co, up to about 9; and Mo, up to about 5.

A structural completion has been described that includes one or more radially expanded and plastically deformed expandable members; wherein one or more of the radially expanded and plastically deformed expandable members are fabricated from a steel alloy comprising the following ranges of weight percentages: C, from about 0.002 to about 0.08; Si, from about 0.009 to about 0.30; Mn, from about 0.10 to about 1.92; P, from about 0.004 to about 0.07; S, from about 0.0008 to about 0.006; Al, up to about 0.04; N, up to about 0.01; Cu, up to about 0.3; Cr, up to about 0.5; Ni, up to about 18; Nb, up to about 0.12; Ti, up to about 0.6; Co, up to about 9; and Mo, up to about 5.

A method for manufacturing an expandable tubular member used to complete a structure by radially expanding and plastically deforming the expandable member has been described that includes forming the expandable tubular member with a ratio of the of an outside diameter of the expandable tubular member to a wall thickness of the expandable tubular member ranging from about 12 to 22.

An expandable member for use in completing a structure by radially expanding and plastically deforming the expandable member has been described that includes an expandable tubular member with a ratio of the of an outside diameter of the expandable tubular member to a wall thickness of the expandable tubular member ranging from about 12 to 22.

A structural completion has been described that includes one or more radially expanded and plastically deformed expandable members positioned within the structure; wherein one or more of the radially expanded and plastically deformed expandable members are fabricated from an expandable tubular member with a ratio of the of an outside diameter of the expandable tubular member to a wall thickness of the expandable tubular member ranging from about 12 to 22.

A method of constructing a structure has been described that includes radially expanding and plastically deforming an expandable member; wherein an outer portion of the wall thickness of the radially expanded and plastically deformed expandable member comprises tensile residual stresses.

A structural completion has been described that includes one or more radially expanded and plastically deformed expandable members; wherein an outer portion of the wall thickness of one or more of the radially expanded and plastically deformed expandable members comprises tensile residual stresses.

A method of constructing a structure using an expandable tubular member has been described that includes strain aging the expandable member; and then radially expanding and plastically deforming the expandable member.

A method for manufacturing a tubular member used to complete a wellbore by radially expanding the tubular member at a downhole location in the wellbore has been described that includes forming a steel alloy comprising a concentration of carbon between approximately 0.002% and 0.08% by weight of the steel alloy.

It is understood that variations may be made to the foregoing without departing from the spirit of the invention. For example, the teachings of the present disclosure may be used to form and/or repair a wellbore casing, a pipeline, or a structural support. Furthermore, the various teachings of the present disclosure may combined, in whole or in part, with various of the teachings of the present disclosure.

Although illustrative embodiments of the invention have been shown and described, a wide range of modification, changes and substitution is contemplated in the foregoing disclosure. In some instances, some features of the present invention may be employed without a corresponding use of the other features. Accordingly, it is appropriate that the appended claims be construed broadly and in a manner consistent with the scope of the invention.

What is claimed is:

1. A method for selecting a solid steel tubular member for suitability for downhole radial expansion and plastic deformation to form a steel wellbore casing on a basis comprising use of an expandability coefficient determined pursuant to a change in diameter of the solid steel tubular member resulting from a stress-strain test performed on the solid steel tubular member, while in a tubular shape, using tensile axial loading.

2. The method of claim 1 wherein selecting the solid steel tubular member is further based on the solid steel tubular member including the percentage by weight of carbon being no less that 0.02% and less than 0.030%.

3. The method of claim 1 wherein selecting the solid steel tubular member is further based on the solid steel tubular member including stress-strain properties in one or more directional orientations.

4. The method of claim 1 wherein selecting the solid steel tubular member is further based on the strength and elongation of the solid steel tubular member.

5. The method of claim 1 wherein selecting the solid steel tubular member is further based on the stress burst rupture of the solid steel tubular member.

6. The method of claim 1 wherein selecting the solid steel tubular member is further based on the strain-hardening exponent and hardness of the solid steel tubular member.

7. The method of claim 1 wherein selecting the solid steel tubular member is further based on the solid steel tubular member including a Charpy V-notch impact value in one or more directional orientations.

8. The method of claim 1 wherein selecting the solid steel tubular member is further based on the stress collapse rupture of the solid steel tubular member.

9. The method of claim 1 wherein selecting the solid steel tubular member is further based on the yield strength of the solid steel tubular member.

10. The method of claim 1 wherein selecting the solid steel tubular member is further based on the ductility of the solid steel tubular member.

11. The method of claim 1 wherein selecting the solid steel tubular member is further based on the toughness of the solid steel tubular member.

12. The method of claim 1 wherein selecting the solid steel tubular member is further based on the solid steel tubular member including a Charpy energy of at least 90 ft-lbs.

13. The method of claim 1 wherein selecting the solid steel tubular member is further based on each of the following ranges of weight percentages of the solid steel tubular member:

Si being from 0.009% to 0.30%;
Mn being from 0.10% to 1.92%;
P being from 0.004% to 0.07%;
S being from 0.0008% to 0.006%;
Al being up to 0.04%;
N being up to 0.01%;
Cu being up to 0.3%;
Cr being up to 0.5%;
Ni being up to 18%;

Nb being up to 0.12%;
Ti being up to 0.6%;
Co being up to 9%; and
Mo being up to 5%.

14. The method of claim 1 wherein the expandability coefficient includes a plastic strain ratio of the steel tubular member.

15. The method of claim 14 wherein the plastic strain ratio includes measurements in multiple anisotropic directions.

16. The method of claim 14 wherein the plastic strain ratio includes a ratio of the strains occurring in the width and length directions of the steel tubular member.

17. The method of claim 1 wherein the expandability coefficient includes a plastic anisotropy of the steel tubular member.

18. The method of claim 1 wherein the expandability coefficient includes a formability anisotropy coefficient F(r).

19. A method comprising:
providing a solid steel tubular member;
performing a stress-strain test on the solid steel tubular member using tensile axial loading while the solid steel tubular member is in a tubular shape, causing a change in diameter of the solid steel tubular member;
determining an expandability coefficient of the solid steel tubular member based on the change in diameter from the stress-strain test;
selecting another solid steel tubular member using the expandability coefficient;
disposing the selected solid steel tubular member in an earthen wellbore; and
radially expanding and plastically deforming the selected solid steel tubular member to form a steel wellbore casing.

20. The method of claim 19 wherein selecting the solid steel tubular member is further based on the solid steel tubular member including the percentage by weight of carbon being no less that 0.02% and less than 0.030%.

21. The method of claim 19 wherein selecting the solid steel tubular member is further based on the solid steel tubular member including stress-strain properties in one or more directional orientations.

22. The method of claim 19 wherein selecting the solid steel tubular member is further based on the strength and elongation of the solid steel tubular member.

23. The method of claim 19 wherein selecting the solid steel tubular member is further based on the stress burst rupture of the solid steel tubular member.

24. The method of claim 19 wherein selecting the solid steel tubular member is further based on the strain-hardening exponent and hardness of the solid steel tubular member.

25. The method of claim 19 wherein selecting the solid steel tubular member is further based on the solid steel tubular member including a Charpy V-notch impact value in multiple directional orientations.

26. The method of claim 19 wherein selecting the solid steel tubular member is further based on each of the following ranges of weight percentages of the solid steel tubular member:
Si being from 0.009% to 0.30%;
Mn being from 0.10% to 1.92%;
P being from 0.004% to 0.07%;
S being from 0.0008% to 0.006%;
Al being up to 0.04%;
N being up to 0.01%;
Cu being up to 0.3%;
Cr being up to 0.5%;
Ni being up to 18%;
Nb being up to 0.12%;
Ti being up to 0.6%;
Co being up to 9%; and
Mo being up to 5%.

27. The method of claim 19 wherein the expandability coefficient includes a plastic strain ratio of the steel tubular member.

28. The method of claim 19 wherein the expandability coefficient includes a plastic anisotropy of the steel tubular member.

29. The method of claim 19 wherein the expandability coefficient includes a formability anisotropy coefficient F(r).

30. A method comprising:
providing a solid steel tubular member;
performing a stress-strain test on the solid steel tubular member using tensile axial loading while the solid steel tubular member is in a tubular shape;
collecting data as a result of the stress-strain test, the data including an outer diameter of the steel tubular member and an inner diameter of the steel tubular member;
determining an expandability coefficient of the solid steel tubular member using the data;
selecting another solid steel tubular member using the expandability coefficient;
disposing the selected solid steel tubular member in an earthen wellbore;
displacing an expansion device through the selected solid steel tubular member while in the wellbore to radially expand and plastically deform the selected solid steel tubular member.

31. The method of claim 30 wherein selecting the solid steel tubular member is further based on the solid steel tubular member including the percentage by weight of carbon being no less that 0.02% and less than 0.030%.

32. The method of claim 30 wherein selecting the solid steel tubular member is (Previously presented) further based on the solid steel tubular member including stress-strain properties in one or more directional orientations.

33. The method of claim 30 wherein selecting the solid steel tubular member is further based on the strength and elongation of the solid steel tubular member.

34. The method of claim 30 wherein selecting the solid steel tubular member is further based on the stress burst rupture of the solid steel tubular member.

35. The method of claim 30 wherein selecting the solid steel tubular member is further based on the strain-hardening exponent and hardness of the solid steel tubular member.

36. The method of claim 30 wherein selecting the solid steel tubular member is further based on the solid steel tubular member including a Charpy V-notch impact value in multiple directional orientations.

37. The method of claim 30 wherein selecting the solid steel tubular member is further based on each of the following ranges of weight percentages of the solid steel tubular member:
Si being from 0.009% to 0.30%;
Mn being from 0.10% to 1.92%;
P being from 0.004% to 0.07%;
S being from 0.0008% to 0.006%;
Al being up to 0.04%;
N being up to 0.01%;
Cu being up to 0.3%;
Cr being up to 0.5%;
Ni being up to 18%;
Nb being up to 0.12%;
Ti being up to 0.6%;

Co being up to 9%; and

Mo being up to 5%.

38. The method of claim 30 wherein the expandability coefficient includes a plastic strain ratio of the steel tubular member.

39. The method of claim 30 wherein the expandability coefficient includes a plastic anisotropy of the steel tubular member.

40. The method of claim 30 wherein the expandability coefficient includes a formability anisotropy coefficient F(r).

41. The method of claim 30 wherein the data includes the strains occurring in the width and length directions of the steel tubular member, and the determining an expandability coefficient includes a ratio of the strains.

42. A method for selecting a solid steel tubular member for suitability for downhole radial expansion and plastic deformation to form a steel wellbore casing on a basis comprising use of an expandability coefficient determined pursuant to a stress-strain test performed on the solid steel tubular member, while in a tubular shape, using tensile axial loading, wherein the expandability coefficient is calculated using the formula:

$$f = \frac{\ln\frac{b_o}{b_k}}{\ln\frac{L_k b_k}{l_o b_o}} \quad \text{Equation 1}$$

where, f—expandability coefficient;

$b_o$ & $b_k$—initial and final tube cross sectional area (inch^2);

$L_o$ & $L_k$—initial and final tube length (inch);

b=(D^2−d^2)/4—cross section tube area;

D=tube outside diameter; and d=tube inside diameter.

43. A method comprising:

providing a solid steel tubular member;

performing a stress-strain test on the solid steel tubular member using tensile axial loading while the solid steel tubular member is in a tubular shape;

determining an expandability coefficient of the solid steel tubular member based on the stress-strain test;

selecting another solid steel tubular member using the expandability coefficient;

disposing the selected solid steel tubular member in an earthen wellbore; and radially expanding and plastically deforming the selected solid steel tubular member to form a steel wellbore casing;

wherein the expandability coefficient is calculated using the formula:

$$f = \frac{\ln\frac{b_o}{b_k}}{\ln\frac{L_k b_k}{l_o b_o}} \quad \text{Equation 1}$$

where, f—expandability coefficient;

$b_o$ & $b_k$—initial and final tube cross sectional area (inch^2);

$L_o$ & $L_k$—initial and final tube length (inch);

b=(D^2−d^2)/4—cross section tube area;

D=tube outside diameter; and d=tube inside diameter.

44. A method comprising:

providing a solid steel tubular member;

performing a stress-strain test on the solid steel tubular member using tensile axial loading while the solid steel tubular member is in a tubular shape;

collecting data as a result of the stress-strain test;

determining an expandability coefficient of the solid steel tubular member using the data;

selecting another solid steel tubular member using the expandability coefficient;

disposing the selected solid steel tubular member in an earthen wellbore;

displacing an expansion device through the selected solid steel tubular member while in the wellbore to radially expand and plastically deform the selected solid steel tubular member;

wherein the expandability coefficient is calculated using the formula:

$$f = \frac{\ln\frac{b_o}{b_k}}{\ln\frac{L_k b_k}{l_o b_o}} \quad \text{Equation 1}$$

where, f—expandability coefficient;

$b_o$ & $b_k$—initial and final tube cross sectional area (inch^2);

$L_o$ & $L_k$—initial and final tube length (inch);

b=(D^2−d^2)/4—cross section tube area;

D=tube outside diameter; and d=tube inside diameter.

45. A method comprising:

providing a solid steel tubular member;

performing a stress-strain test on the solid steel tubular member using tensile axial loading while the solid steel tubular member is in a tubular shape;

collecting data as a result of the stress-strain test;

determining an expandability coefficient of the solid steel tubular member using the data;

selecting another solid steel tubular member using the expandability coefficient;

disposing the selected solid steel tubular member in an earthen wellbore;

displacing an expansion device through the selected solid steel tubular member while in the wellbore to radially expand and plastically deform the selected solid steel tubular member;

wherein the data includes a force measurement, an outer diameter of the steel tubular member, an inner diameter of the steel tubular member, or a combination thereof, and the determining an expandability coefficient includes calculating an anisotropy of the steel tubular member using a ratio of the data.

* * * * *